US006638732B1

(12) United States Patent
Evans

(10) Patent No.: US 6,638,732 B1
(45) Date of Patent: Oct. 28, 2003

(54) MUTANTS OF GREEN FLUORESCENT PROTEIN

(75) Inventor: Krista Evans, Germantown, MD (US)

(73) Assignee: Invitrogen Corporation, Carlsbad, CA (US)

( * ) Notice: Subject to any disclaimer, the term of this patent is extended or adjusted under 35 U.S.C. 154(b) by 0 days.

(21) Appl. No.: 09/472,065

(22) Filed: Dec. 23, 1999

Related U.S. Application Data

(63) Continuation of application No. 08/970,762, filed on Nov. 14, 1997, now abandoned.
(60) Provisional application No. 60/030,935, filed on Nov. 15, 1996.

(51) Int. Cl.[7] .................. C12P 21/06; C07K 14/435; C12N 1/21; C12N 15/52; C07H 21/04
(52) U.S. Cl. ................ 435/69.1; 435/252.3; 435/320.1; 435/325; 435/410; 536/23.5; 530/350
(58) Field of Search .................... 435/252.3, 320.1, 435/69.1, 325, 410; 536/23.5; 530/350

(56) References Cited

U.S. PATENT DOCUMENTS

| | | | |
|---|---|---|---|
| 5,491,084 A | 2/1996 | Chalfie et al. | 435/189 |
| 5,625,048 A | 4/1997 | Tsien et al. | 536/23.4 |
| 5,777,079 A | 7/1998 | Tsien et al. | 530/350 |
| 5,804,387 A * | 9/1998 | Cormack et al. | 435/6 |
| 5,968,738 A | 10/1999 | Anderson et al. | 435/6 |
| 5,994,077 A | 11/1999 | Valdivia et al. | 435/6 |
| 6,027,881 A * | 2/2000 | Pavlakis et al. | 435/6 |
| 6,054,321 A | 4/2000 | Tsien et al. | 436/86 |
| 6,066,476 A | 5/2000 | Tsien et al. | 435/69.7 |
| 6,077,707 A | 6/2000 | Tsien et al. | 435/325 |
| 6,124,128 A | 9/2000 | Tsien et al. | 435/252.33 |
| 6,146,826 A | 11/2000 | Chalfie et al. | 435/6 |
| 6,172,188 B1 * | 1/2001 | Thastrup et al. | 530/350 |
| 6,319,669 B1 | 11/2001 | Tsien et al. | 435/6 |
| 6,403,374 B1 | 6/2002 | Tsien et al. | 435/325 |

FOREIGN PATENT DOCUMENTS

| | | |
|---|---|---|
| EP | 1 104 769 A2 | 6/2001 |
| WO | WO 96/23810 A1 | 8/1996 |
| WO | WO 97/11094 | 3/1997 |
| WO | WO 98/14605 | 4/1998 |
| WO | WO 01/98338 A2 | 12/2001 |
| WO | WO 02/085936 A2 | 10/2002 |

OTHER PUBLICATIONS

Tsien, R.Y., "The Green Fluorescent Protein," *Annu. Rev. Biochem* 67:509–544 (1998).

Chalfie, et al., "Green Fluorescent Protein as a Marker for Gene Expression," *Science* 263:802–805 (Feb. 1994).

Cody, C.W., et al., "Chemical Structure of the Hexapeptide Chromophore of the Aequorea Green–Fluorescent Protein," *Biochemistry* 32:1212–1218 (Feb. 1993).

Cormack, B., et al., "Isolation of FACS–Optimized Variants of Green fluroescent Protein," *CLONTECHniques*, p. 21 (Apr. 1996).

Cormack, B.P., et al., "FACS–Optimized Mutants of the Green Fluoescent Protein (GFP)," *Gene* 173:33–38 (Jul. 1996).

Crameri, A., et al., "Improved Green Fluorescent Protein by Molecular Evolution using DNA Shuffling," *Nature Biotechnol.* 14:315–319 (Mar. 1996).

Delagrave, S., et al., "Red–Shifted Excitation Mutants of the Green Fluorescent Protein," *BioTechnology* 13:151–154 (Feb. 1995).

Ehrig, T., et al., "Green–fluorescent Protein Mutants with Altered Fluorescence Excitation Spectra," *FEBS Lett.* 367:163–166 (Jun. 1995).

Evans, K., et al., "pGreen Lantern™–1, a Superior Green Fluorescent Protein Mammalian Cell Transfection Reporter," *FOCUS* 18:40–43 (Jul. 1996).

Heim, R., et al., "Wavelength Mutations and Posttranslational Autoxidation of green Fluorescent Protein," *Proc. Natl. Acad. Sci. USA* 91:12501–12504 (Dec. 1994).

Heim, R., et al., "Improved green Fluorescence," *Nature* 373:663–664 (Feb. 1995).

Heim, R., and Tsien, R.Y., "Engineering Green Fluorescent Protein for Improved Brightness, Longer Wavelengths and Fluorescence Resonance Energy Transfer," *Curr. Biol.* 6:178–182 (Feb. 1996).

Marshall, J., et al., "The Jellyfish Green Fluorescent Protein: A New Tool for Studying Ion Channel Expression and Function," *Neuron* 14:211–215 (Feb. 1995).

(List continued on next page.)

Primary Examiner—Elizabeth Slobodyansky
(74) Attorney, Agent, or Firm—Sterne, Kessler, Goldstein & Fox P.L.L.C.

(57) ABSTRACT

The present invention provides mutants of the Green Fluorescent Protein (GFP) of *Aequorea victoria*. Specifically provided by the present invention are nucleic acid molecules encoding mutant GFPs, the mutant GFPs encoded by these nucleic acid molecules, vectors and host cells comprising these nucleic acid molecules, and kits comprising one or more of the above as components. The invention also provides methods for producing these mutant GFPs. The fluorescence of these mutants is observable using fluorescein optics, making the mutant proteins of the present invention available for use in techniques such as fluorescence microscopy and flow cytometry using standard FITC filter sets. In addition, certain of these mutant proteins fluoresce when illuminated by white light, particularly when expressed at high levels in prokaryotic or eukaryotic host cells or when present in solution or in purified form at high concentrations. The mutant GFP sequences and peptides of the present invention are useful in the detection of transfection, in fluorescent labeling of proteins, in construction of fusion proteins allowing examination of intracellular protein expression, biochemistry and trafficking, and in other applications requiring the use of reporter genes.

23 Claims, 12 Drawing Sheets

OTHER PUBLICATIONS

Misteli, T., and Spector, D.L., "Applications of the Green Fluorescent Protein in Cell Biology and Biotechnology," *Nature Biotechnol.* 15:961–964 (Oct. 1997).

Ormö, M., et al., "Crystal Structure of the *Aequorea victoria* Green Fluorescent Protein," *Science* 273:1392–1395 (Sep. 1996).

Palm, G.L., et al., "The structural basis for spectral variations in green fluorescent protein," *Nature Struct. Biol.* 4:361–365 (May 1997).

Prasher, D.C., et al., "Primary structure of the *Aequorea victoria* green–fluorescent protein," *Gene* 111:229–233 (Feb. 1992).

Rizzuto, R., et al., "Double labeling of subcellular structures with organelle–targeted GFP mutants in vivo," *Curr. Biol.* 6:183–188 (Feb. 1996).

Wang, S., and Hazerlrigg, T., "Implications for bcd mRNA localization from spatial distribution of exu protein in Drosophila oogenesis," *Nature* 369:400–403 (Jun. 1994).

Ward, W.W., and Cormier, M.J., "Energy transfer via protein–protein interaction in Renilla bioluminescence," *Photochem. Photobiol.* 27:389–396 (1978).

Yang, F., et al., "The molecular structure of green fluorescent protein," *Nature Biotehcnol.* 14:1246–1251 (Oct. 1996).

Yokoe, H., and Meyer, T., "Spatial dynamics of GFP–tagged proteins investigated by local fluorescence enhancement," *Nature Biotechnol.* 14:1252–1256 (Oct. 1996).

Zolotukhin, S., et al., "A 'Humanized' Green Fluorescent Protein cDNA Adapted for High–Level Expression in Mammalian Cells," *J. Virol.* 70:4646–4654 (Jul. 1996).

Clontech, Inc., Palo Alto, California, "Living Colors™ Enhanced GFP Vectors. The brightest GFP chromophore variant for maximal sensitivity in mammalian cells," CLONTECHniques, pp. 2–3 (Apr. 1996).

\* cited by examiner

```
ATG AGC AAG GGC GAG GAA CTG TTC ACT GGC GTG GTC CCA ATT CTC GTG
Met Ser Lys Gly Glu Glu Leu Phe Thr Gly Val Val Pro Ile Leu Val
 1           5                      10                      15

GAA CTG GAT GGC GAT GTG AAT GGG CAC AAA TTT TCT GTC AGC GGA GAG
Glu Leu Asp Gly Asp Val Asn Gly His Lys Phe Ser Val Ser Gly Glu
             20                      25                  30

GGT GAA GGT GAT GCC ACA TAC GGA AAG CTC ACC CTG AAA TTC ATC TGC
Gly Glu Gly Asp Ala Thr Tyr Gly Lys Leu Thr Leu Lys Phe Ile Cys
         35                      40                  45

ACC ACT GGA AAG CTC CCT GTG CCA TGG CCA ACA CTG GTC ACT ACC TTC
Thr Thr Gly Lys Leu Pro Val Pro Trp Pro Thr Leu Val Thr Thr Phe
     50                      55                      60

ACC TAT GGC GTG CAG TGC TTT TCC AGA TAC CCA GAC CAT ATG AAG CAG
Thr Tyr Gly Val Gln Cys Phe Ser Arg Tyr Pro Asp His Met Lys Gln
 65                      70                      75          80

CAT GAC TTT TTC AAG AGC GCC ATG CCC GAG GGC TAT GTG CAG GAG AGA
His Asp Phe Phe Lys Ser Ala Met Pro Glu Gly Tyr Val Gln Glu Arg
                 85                      90                  95

ACC ATC TTT TTC AAA GAT GAC GGG AAC TAC AAG ACC CGC GCT GAA GTC
Thr Ile Phe Phe Lys Asp Asp Gly Asn Tyr Lys Thr Arg Ala Glu Val
             100                     105             110

AAG TTC GAA GGT GAC ACC CTG GTT AAT AGA ATC GAG TTG AAG GGC ATT
Lys Phe Glu Gly Asp Thr Leu Val Asn Arg Ile Glu Leu Lys Gly Ile
         115                     120             125

GAC TTT AAG GAA GAT GGA AAC ATT CTC GGC CAC AAG CTG GAA TAC AAC
Asp Phe Lys Glu Asp Gly Asn Ile Leu Gly His Lys Leu Glu Tyr Asn
     130                     135                 140

TAT AAC TCC CAC AAT GTG TAC ATC ATG GCC GAC AAG CAA AAG AAT GGC
Tyr Asn Ser His Asn Val Tyr Ile Met Ala Asp Lys Gln Lys Asn Gly
145                 150                 155                 160

ATC AAG GTC AAC TTC AAG ATC AGA CAC AAC ATT GAG GAT GGA TCC GTG
Ile Lys Val Asn Phe Lys Ile Arg His Asn Ile Glu Asp Gly Ser Val
                 165                 170             175

CAG CTG GCC GAC CAT TAT CAA CAG AAC ACT CCA ATC GGC GAC GGC CCT
Gln Leu Ala Asp His Tyr Gln Gln Asn Thr Pro Ile Gly Asp Gly Pro
             180                 185             190

GTG CTC CTC CCA GAC AAC CAT TAC CTG TCC ACC CAG TCT GCC CTG TCT
Val Leu Leu Pro Asp Asn His Tyr Leu Ser Thr Gln Ser Ala Leu Ser
         195                 200             205

AAA GAT CCC AAC GAA AAG AGA GAC CAC ATG GTC CTG CTG GAG TTT GTG
Lys Asp Pro Asn Glu Lys Arg Asp His Met Val Leu Leu Glu Phe Val
     210                 215                 220

ACC GCT GCT GGG ATC ACA CAT GGC ATG GAC GAG CTG TAC AAG TAA
Thr Ala Ala Gly Ile Thr His Gly Met Asp Glu Leu Tyr Lys  *
225             230                 235

(SEQ ID NOs:1, 2)
```

FIG. 1

```
ATG AGT AAA GGA GAA GAA CTT TTC ACT GGA GTT GTC CCA ATT CTT GTT      48
Met Ser Lys Gly Glu Glu Leu Phe Thr Gly Val Val Pro Ile Leu Val
1               5                   10                  15

GAA TTA GAT GGT GAT GTT AAT GGG CAC AAA TTT TCT GTC AGT GGA GAG      96
Glu Leu Asp Gly Asp Val Asn Gly His Lys Phe Ser Val Ser Gly Glu
            20                  25                  30

GGT GAA GGT GAT GCA ACA TAC GGA AAA CTT ACC CTT AAA TTT ATT TGC     144
Gly Glu Gly Asp Ala Thr Tyr Gly Lys Leu Thr Leu Lys Phe Ile Cys
        35                  40                  45

ACT ACT GGA AAA CTA CCT GTT CCA TGG CCA ACA CTT GTC ACT ACT TTC     192
Thr Thr Gly Lys Leu Pro Val Pro Trp Pro Thr Leu Val Thr Thr Phe
    50                  55                  60

TCT TAT GGT GTT CAA TGC TTT TCA AGA TAC CCA GAT CAT ATG AAA CAG     240
Ser Tyr Gly Val Gln Cys Phe Ser Arg Tyr Pro Asp His Met Lys Gln
65                  70                  75                  80

CAT GAC TTT TTC AAG AGT GCC ATG CCC GAA GGT TAT GTA CAG GAA AGA     288
His Asp Phe Phe Lys Ser Ala Met Pro Glu Gly Tyr Val Gln Glu Arg
                85                  90                  95

ACT ATA TTT TTC AAA GAT GAC GGG AAC TAC AAG ACA CGT GCT GAA GTC     336
Thr Ile Phe Phe Lys Asp Asp Gly Asn Tyr Lys Thr Arg Ala Glu Val
            100                 105                 110

AAG TTT GAA GGT GAT ACC CTT GTT AAT AGA ATC GAG TTA AAA GGT ATT     384
Lys Phe Glu Gly Asp Thr Leu Val Asn Arg Ile Glu Leu Lys Gly Ile
        115                 120                 125

GAT TTT AAA GAA GAT GGA AAC ATT CTT GGA CAC AAA TTG GAA TAC AAC     432
Asp Phe Lys Glu Asp Gly Asn Ile Leu Gly His Lys Leu Glu Tyr Asn
    130                 135                 140

TAT AAC TCA CAC AAT GTA TAC ATC ATG GCA GAC AAA CAA AAG AAT GGA     480
Tyr Asn Ser His Asn Val Tyr Ile Met Ala Asp Lys Gln Lys Asn Gly
145                 150                 155                 160

ATC AAA GTT AAC TTC AAA ATT AGA CAC AAC ATT GAA GAT GGA AGC GTT     528
Ile Lys Val Asn Phe Lys Ile Arg His Asn Ile Glu Asp Gly Ser Val
                165                 170                 175

CAA CTA GCA GAC CAT TAT CAA CAA AAT ACT CCA ATT GGC GAT GGC CCT     576
Gln Leu Ala Asp His Tyr Gln Gln Asn Thr Pro Ile Gly Asp Gly Pro
            180                 185                 190

GTC CTT TTA CCA GAC AAC CAT TAC CTG TCC ACA CAA TCT GCC CTT TCG     624
Val Leu Leu Pro Asp Asn His Tyr Leu Ser Thr Gln Ser Ala Leu Ser
        195                 200                 205

AAA GAT CCC AAC GAA AAG AGA GAC CAC ATG GTC CTT CTT GAG TTT GTA     672
Lys Asp Pro Asn Glu Lys Arg Asp His Met Val Leu Leu Glu Phe Val
    210                 215                 220

ACA GCT GCT GGG ATT ACA CAT GGC ATG GAT GAA CTA TAC AAA             714
Thr Ala Ala Gly Ile Thr His Gly Met Asp Glu Leu Tyr Lys
225                 230                 235

TAA                                                                 717
                    (SEQ ID NOs:3, 4)
```

FIG.2

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Cys
    50                  55                  60

Ala Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

(SEQ ID NO:5)

FIG.3

Met Ser Lys Gly Glu Glu Leu Phe Thr Gly Val Val Pro Ile Leu Val
1           5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Met
    50                  55                  60

Ala Tyr Gly Val Gln Cys Phe Ser Arg Tyr Pro Asp His Met Lys Gln
65              70                  75                      80

His Asp Phe Phe Lys Ser Ala Met Pro Glu Gly Tyr Val Gln Glu Arg
            85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
        130                 135                 140

Tyr Asn Ser His Asn Val Tyr Ile Met Ala Asp Lys Gln Lys Asn Gly
145             150                 155                     160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225             230                 235

(SEQ ID NO:6)

FIG.4

MUTANTS OF GREEN FLUORESCENT PROTEIN

CROSS REFERENCE TO RELATED APPLICATION

This application is a continuation of U.S. application Ser. No. 08/970,762, filed Nov. 14, 1997, now abandoned which claims priority to U.S. Provisional Application No. 60/030,935, filed Nov. 15, 1996, the contents of which are entirely incorporated herein by reference.

BACKGROUND OF THE INVENTION

1. Field of the Invention

This invention is in the fields of molecular and cellular biology. More particularly, the invention is directed to mutants of the genes encoding Green Fluorescent Protein (GFP) and the proteins encoded by these mutants. The mutant GFPs are used to allow detection of eukaryotic and prokaryotic cells transfected or transformed with extrinsic genes, and to label proteins of interest to facilitate their localization within viable cells.

2. Related Art

Transfection of Foreign Genes

To study the function of a gene, a technique that is commonly employed is the transfer of the gene into a new cellular environment. This process, called "transfection," provides several advantages to the genetic scientist. For example, the cellular protein encoded by the gene can often be more easily studied by transferring the gene into a cell or organism that normally does not produce the protein, and then examining the effect of this protein on the host cell. The existence and function of regulatory genetic sequences (e.g., promoters, inhibitors and enhancers) may be elucidated by transfection of foreign genes into cells containing the regulatory sequences. The transfer of non-native or altered genes into a host cell also allows for large-scale production of the proteins encoded by the genes, a process upon which much of the current biotechnology industry is based. Transfection of plant embryos with foreign genes has provided genetically engineered plants that are more resistant to adverse environmental conditions or that are more nutritionally rich. Finally, gene transfer methods allow the introduction of new or mutated genes into whole organisms. This latter capability provides the opportunity for the construction of stable models of mammalian diseases, for large-scale production of proteins in the milk of transgenic lactating animals, and for the possibility of genetic therapy for certain diseases.

A variety of techniques has been used to transfect non-native genes into cells (reviewed in Sambrook, J., et al., *Molecular Cloning, a Laboratory Manual*, 2nd Ed., Cold Spring Harbor, N.Y.: Cold Spring Harbor Laboratory Press, pp. 16.30–16.55 (1989); Watson, J. D., et al., *Recombinant DNA*, 2nd Ed, New York: W. H. Freeman and Co., pp. 213–234 (1992)). These techniques include biological methods such as the use of viruses (e.g., adenovirus or certain retroviruses for mammalian cells, baculovirus for insect cells and bacteriophages for bacterial cells) or bacteria (e.g., Agrobacterium for plant cells), chemical methods such as calcium phosphate precipitation, DEAE-dextran-mediated endocytosis or liposome-mediated transfection, and physical methods such as electroporation or direct microinjection. For transfection of mammalian cells, the techniques most commonly employed currently are virus-mediated transfection, lipofection and electroporation.

Detection of Gene Transfer

Regardless of the method used, however, simply attempting to transfect a cell does not guarantee that a majority (or even any) of the target cells will take up and/or express the exogenous DNA. Indeed, it has been suggested that the success rate of even the most optimal techniques used for transfection results in stable transfer of exogenous DNA is far less than 1% (Watson, J. D., et al., *Recombinant DNA*, 2nd Ed., New York: W. H. Freeman and Co., pp. 216, 218 (1992)). Thus, it is usually critical to determine which target cells have received and/or incorporated the gene(s) being transfected, for which a number of methodologies have been used.

Expression

The most obvious of these methods is to simply examine the target cells for expression of the exogenous gene. In this method, the transfected cells are grown in vitro and assayed for the presence of the protein encoded by the transferred gene. These assays are usually accomplished using immunological techniques such as Western blotting, ELISA or RIA. This type of technique is only useful, however, if the protein is produced in relatively high amounts (generally at the microgram level or above) and if suitable antibodies are available, neither of which is the case for some transfected genes.

In those cases where protein expression cannot be examined, incorporation of exogenous genes can be determined by assaying the target cells for production of the mRNAs corresponding to the transferred genes. One very common technique for this determination is Northern blotting (Alwine, J. C., et al., *Proc. Natl. Acad Sci. USA* 74:5350–5354, 1977), in which RNA molecules are isolated from cells, separated by gel electrophoresis and electroblotted onto a solid support (e.g., nitrocellulose or nylon). The solid support is then overlaid with radiolabelled cDNAs corresponding to the transfected gene, which hybridize on the solid support to their complementary mRNAs. After exposing the blot to photographic film, the samples containing the expressed transgene are easily determined. While this method is more sensitive than those directly measuring protein expression, Northern blotting still relies on actual expression of the gene by the target cells, which is not always the case.

Selection

Another method for determining gene transfer, alternative to directly measuring gene expression, is to examine the effect of the gene on the transfected cells. For example, some transfected genes will confer upon their host cells the ability to grow in selective culture media or under some other environmental stress which non-transfected cells cannot tolerate. Genes of interest are often engineered into sequences conferring, for example, antibiotic resistance upon the recipient cells. Transfectants with these constructs will thus carry not only the gene of interest but also the antibiotic resistance gene which allows them to grow in antibiotic-containing media. Since non-transfected cells will not possess this resistance, any cell able to grow in media containing antibiotic will contain the resistance marker (the so-called "selectable marker") and the transgene that is linked to it. Selectable markers commonly used in such an approach are the neomycin (neo), ampicillin (amp) and hygromycin (hyg) resistance genes.

In the same way, selectable markers conferring on the transfected cells a metabolic advantage (e.g., ability to grow in nutrient-deficient media) have been used successfully. Examples of these types of selectable markers include thymidine kinase (Bacchetti, S., and Graham, F. L., *Proc. Natl. Acad. Sci. USA* 74:1590–1594 (1977); Wigler, M., et al., *Cell* 11:223–232 (1977)) and xanthine-guanine phosphoribosyltransferase (Mulligan, R. C., and Berg, P., *Proc. Natl.*

*Acad Sci. USA* 78:2072–2076 (1981)), which impart to their recipients the ability to grow, using metabolic rescue pathways encoded by the marker genes, in media that inhibit vital metabolic pathways in non-transfected cells. Again, any cells able to grow in such media will contain the transgene linked to the marker gene.

Selection methods such as these often require weeks of culturing of the cells, continuously under selective pressure, to provide a relatively pure population of stable transfectants. Many uses of transfected cells, however, are conducted within hours of transfection, far too soon to determine transfection success using either the expression or selection methods described above. These types of applications are facilitated by a third approach—the use of "reporter genes".

Reporter Genes

Reporter genes are analogous to selectable markers in that they are co-transfected into recipient cells with the gene of interest, and provide a means by which transfection success may be determined. Unlike selectable markers, however, reporter genes typically do not confer any particular advantage to the recipient cell. Instead reporter genes, as their name implies, indicate to the observer (via some phenotypic activity) which cells have incorporated the reporter gene and thus the gene of interest to which it is linked. A number of reporter genes have been used, including those operating by biochemical or fluorescent mechanisms, each with its own advantages and limitations.

Biochemical Reporter Genes

Some commonly used reporter genes encode enzymes or other biochemical markers which, when active in the transfected cells, cause some visible change in the cells or their environment upon addition of the appropriate substrate. Two examples of this type of reporter sequence are the *E. coli* genes lacZ (encoding β-galactosidase or "β-gal") and gusA or iudA (encoding β-glucuronidase or "β-glu"); the former is often used as a reporter gene in animal cells (Hall, C. V., et al., *J. Mol. Appl. Genet* 2:101–109 (1983); Cui, C., et al., *Trangenic Res.* 3:182–194 (1994)), the latter in plant cells (Jefferson, R. A., *Nature* 342:837–838 (1989); Watson, J. D., et al., *Recombinant DNA*, 2nd Ed., New York: W. H. Freeman and Co., pp. 281–282 (1992); Hull, G. A., and Devic, M., *Meth. Mol. Biol.* 49:125–141 (1995)). These bacterial sequences are useful as reporter genes because the recipient cells, prior to transfection, express extremely low levels (if any) of the enzyme encoded by the reporter gene. When transfected cells expressing the reporter gene are incubated with an appropriate substrate (e.g., X-gal for β-gal or X-gluc for β-glu), a colored or fluorescent product is formed which can be detected and quantitated histochemically or fluorimetrically.

Another often-used reporter gene is the bacterial gene encoding chloramphenicol acetyltransferase (CAT), which catalyzes the addition of acetyl groups to the antibiotic chloramphenicol (Gorman, C. M., et al., *Mol. Cell. Biol.* 2:1044–1051 (1982); Neumann, J. R., et al., *BioTechniques* 5:444–446 (1987); Eastman, A, *BioTechniques* 5:730–732 (1987); Felgner, P. L., et al., *Ann. N.Y. Acad Sci.* 772:126–139 (1995)). After transfection, recipient cells are lysed and the lysates are incubated with radiolabelled chloramphenicol and an acetyl donor such as acetyl-CoA, or with unlabeled chloramphenicol and radiolabeled acetyl-CoA (Sleigh, M. J., *Anal. Biochem.* 156:251–256 (1986)). If expressed in the cells, CAT transfers acetyl groups to chloramphenicol, which is then easily assayed by chromatographic techniques, thereby giving an indication of the incorporation of the co-transfected gene of interest by the recipient cells.

Using reporter genes in this way, populations of cells, or even single cells, can be rapidly assayed for their incorporation of the exogenous gene linked to the reporter gene. Since they do not rely directly on the expression of the gene of interest, assays of transfection success using reporter genes are usually simpler and more sensitive than those measuring mRNA or protein production from the transgene (Watson, J. D., et al., *Recombinant DNA*, 2nd Ed., New York: W. H. Freeman and Co., p. 155 (1992)). However, the use of reporter genes is severely limited in that it usually requires sacrifice (fixation) of the cells prior to assay, and therefore cannot be used for assaying living cells or cultures. Thus, alternative means for determining the incorporation of the transgene in viable cells have been developed.

Fluorescent Reporter Genes

An example of viable reporter genes that are rapidly gaining widespread use are those that are fluorescence-based. These genes encode proteins which are either naturally fluorescent or which convert a substrate from nonfluorescent to fluorescent. Assays using this type of reporter gene are non-destructive and, owing to the availability of sophisticated fluorescence detection systems, are often more sensitive than biochemical reporter gene assays.

One example of a fluorescence reporter gene is the luciferin-luciferase system (Bronstein, I., et al., *Anal. Biochem.* 219:169–181 (1994)). This system utilizes the gene for luciferase, an ATPase enzyme isolated from fireflies (Gould, S. J., and Subramani, S., *Anal. Biochem.* 175:5–13 (1988)) and other beetles (Wood, K. V., et al., *J. Biolumin. Chemilumin.* 4:289–301 (1989)), or from certain bioluminescent bacteria (Stewart, G. S., and Williams, P., *J. Gen. Microbiol.* 138:1289–1300 (1992); Langridge, W., et al., *J. Biolumin. Chemilumin.* 9:185–200 (1994)). For use as a reporter gene, the luciferase gene is placed into a vector also containing the gene of interest, or separate vectors containing the luciferase gene and the gene of interest are mixed together. Cells are then transfected with the vector(s) and treated with the luciferase substrate luciferin which is rendered luminescent (and impermeant) intracellularly by the action of the luciferase. Cells containing the luciferase gene, and thus the gene of interest linked to it, can then be rapidly and sensitively observed using luminescence detectors such as luminometers.

To provide a further increase in sensitivity, attempts have been made to use genes from certain cyanobacteria which encode naturally fluorescent phycobiliproteins such as phycoerythrin and phycocyanin. These proteins are among the most highly fluorescent known (Oi, V. T., et al., *J. Cell Biol.* 93:981–986 (1982)), and systems have been developed that are able to detect the fluorescence emitted from as little as one phycobiliprotein molecule (Peck, K., et al., *Proc. Natl. Acad. Sci. USA* 86:4087–4091 (1989)). Phycobiliproteins also have the advantage of being naturally fluorescent, thus eliminating the time-consuming steps of the addition of exogenous substrates for their detection as is required for luciferase and biochemical reporter genes. However, the phycobiliproteins have proven extremely difficult to engineer into gene constructs in such a way as to maintain their fluorescence (Heim, R., et al., *Proc. Natl. Acad. Sci. USA* 91:12501–12504 (1994)), and thus are not commonly used as reporter genes in assaying the transfection of mammalian cells.

Thus, the ideal reporter gene would encode a naturally fluorescent protein (for ease of use following transfection) that is highly fluorescent (for increased sensitivity) and easily engineered (for maintenance of fluorescence). Such a system has recently been developed, using the Green Fluorescent Proteins (GFPs) isolated from certain marine cnidarians.

GFP

Overview

GFPs are involved in bioluminescence in a variety of marine invertebrates, including jellyfish such as Aequorea spp. (Morise, H., et al., *Biochemistry* 13:2656–2662 (1974); Prendergast, F. G., and Mann, K. G., *Biochemistry* 17:3448–3453 (1978); Ward, W. W., *Photochem. Photobiol. Rev.* 4:1–57 (1979) and the sea pansy *Renilla reniformis* (Ward, W. W., and Cormier, M. J., *Photochem. Photobiol.* 27:389–396 (1978); Ward, W. W., et al., *Photochem. Photobiol.* 31:611–615 (1980)). The GFP isolated from *Aequorea victoria* has been cloned and the primary amino acid structure has been deduced (FIG. 1; Prasher, D. C., et al., *Gene* 111:229–233 (1992)) (SEQ ID NOs:1, 2). The chromophore of *A. victoria* GFP is a hexapeptide composed of amino acid residues 64–69 in which the amino acids at positions 64–67 (serine, tyrosine and glycine) form a heterocyclic ring (Prasher, D. C., et al., *Gene* 111:229–233 (1992); Cody, C. W., et al., *Biochemistry* 32:1212–1218 (1993)). Resolution of the crystal structure of GFP has shown that the chromophore is contained in a central α-helical region surrounded by an 11-stranded β-barrel (Ormo, M., et al., *Science* 273:1392–1395 (1996); Yang, F., et al., *Nature Biotech.* 14:1246–1251 (1996)). Upon purification, native GFP demonstrates an absorption maximum at 395 nanometers (nm) and an emission maximum at 509 nm (Morise, H., et al., *Biochemistry* 13:2656–2662 (1974); Ward, W. W., et al., *Photochem. Photobiol.* 31:611–615 (1980)) with exceptionally stable and virtually non-photobleaching fluorescence (Chalfie, M., et al., *Science* 263:802–805 (1994)).

While GFP has been used as a fluorescent label in protein localization and conformation studies (Heim, R., et al., *Proc. Natl. Acad Sci. USA* 91:1250–1254 (1994); Yokoe, H., and Meyer, T., *Nature Biotech.* 14:1252–1256 (1996)), it has gained increased attention in the field of molecular genetics since the demonstration of its utility as a reporter gene in transfected prokaryotic and eukaryotic cells (Chalfie, M., et al., *Science* 263:802–805 (1994); Heim, R., et al., *Proc. Natl. Acad. Sci. USA* 91:1250–1254 (1994); Wang, S., and Hazelrigg, T., *Nature* 369:400–403 (1994)). GFP has also been used in fluorescence resonance energy transfer studies of protein-protein interactions (Heim, R., and Tsien, R. Y., *Curr. Biol.* 6:178–182 (1996)). Since GFP is naturally fluorescent, exogenous substrates and cofactors are not necessary for induction of fluorescence, thus providing GFP an advantage over the biochemical, luminescent and other fluorescent reporter genes described above. Visualization of GFP fluorescence does not require the fixation steps necessary with biochemical reporters such as β-gal and β-glu, nor does it require extraction from the cell prior to assay as may be required with luciferase; thus, GFP is suitable for use in procedures requiring continued viability of transfected cells. In addition, since the GFP cDNA containing the complete coding region is less than 1 kilobase in size (Prasher, D. C., et al., *Gene* 111:229–233 (1992)), it is easily manipulated and inserted into a variety of vectors for use in creating stable transfectants (Chalfie, M., et al., *Science* 263:802–805 (1994)).

Despite these advantages, however, the use of wildtype GFP has a few limitations. For example, the excitation and emission maxima of wildtype GFP are not within the range of wavelengths of standard fluorescence optics (at which GFP demonstrates relatively low quantum yield (i.e., low intensity of fluorescence)). In addition, GFP shows low efficiency of transcription in mammalian cells upon transfection and is packaged into low-solubility inclusion bodies in bacteria (thus providing difficulty in purification). These limitations have been overcome to a limited extent via the introduction of selected point mutations into the sequence of wildtype GFP.

GFP Mutants

One of the earliest mutation studies of GFP, in which the tyrosine residue at position 66 in the wildtype protein ("wt-GFP") was replaced with a histidine residue, resulted in a mutant protein which fluoresced blue instead of green when excited with ultraviolet (UV) light (Heim, R., et al., *Proc. Natl. Acad. Sci. USA* 91:1250–1254 (1994)). This mutant protein not only provided a capacity for two distinguishable wavelengths for use in studies comparing independent proteins and gene expression events, but also demonstrated that single point mutations in GFP could induce drastic changes in the photochemistry of the protein. Three other sets of specific point mutations have been shown to increase the excitation and emission maxima of GFP such that they fall well within the range of standard fluorescein optics (Ehrig, T., et al., *FEBS Letts.* 367:163–166 (1995); Delagrave, S., et al., *Bio/Technology* 13:151–154 (1995); Heim, R., and Tsien, R., *Curr. Biol.* 6:178–182 (1996)), thus permitting the use of GFP with standard laboratory fluorescence detection systems. The problem of low quantum yield by wt-GFP has been partially addressed by mutating the serine residue at position 65 to a threonine ("S65T"), either without (Heim, R., et al., *Proc. Natl. Acad Sci. USA* 91:12501–12504 (1994)) or with (Cormack, B., et al., *Gene* 173:33–38 (1996)) a concomitant mutation at position 64, or by mutating other residues in the non-chromophore region (Crameri, A., et al., *Nature Biotech.* 14:315–319 (1996)). The S65T mutation also appears to improve the rate of fluorophore formation in transfected cells by approximately four-fold over wt-GFP, thus allowing earlier and more sensitive detection of transfection with this mutant than with wt-GFP (Heim, R., et al., *Proc. Natl. Acad. Sci. USA* 91:1250–1254 (1994)). By combining the S65T mutation with a mutation at position 64 replacing phenylalanine with leucine, approximately 90% of the mutant GFP expressed in bacteria is soluble, thus improving protein purification and yields (Cormack, B., et al., *Gene* 173:33–38 (1996)). Another series of mutations results in a mutant fusion GFP consisting of linked blue- and green-fluorescing proteins which have proven useful in studies of protein localization, targeting and processing (Heim, R., and Tsien, R. Y., *Curr. Biol.* 6:178–182 (1996)). Analogously, chimeric constructs comprising GFP linked to other proteins have been used in studies of ion channel expression and function (Marshall, J., et al., *Neuron* 14:211–215 (1995)), and in organelle targeting studies where they have provided a means for selectively and distinctively labeling the organelles of living cells (Rizzuto et al., *Curr. Biol.* 6:183–188 (1996)). Finally, by combining the S65T mutation with other mutations throughout the nonchromophore regions of the wt-GFP gene, a "humanized" mutant GFP (SEQ ID NOs:3, 4) has been produced that not only shows a significant increase in fluorescence intensity and rate of fluorophore formation over wt-GFP (via the S65T mutation) but also demonstrates a 22-fold increased expression efficiency in mammalian cells (Evans, K., et al., *FOCUS* 18(2):40–43 (1996); Zolotukhin, S., et al., *J. Virol.* 70:4646–4654 (1996)). This humanization was achieved via 92 base substitutions (in 88 codons) to the wt-GFP gene which were amino acid-conservative and which were made to provide a pattern of codon usage more closely resembling that of mammalian cells, as opposed to the jellyfish codon patterns found in the wt-GFP gene which are less efficiently translated in mammalian cells. A summary of these GFP chromophore mutants is presented in Table 1.

TABLE 1

GFP Chromophore Mutants.

Amino Acid Residue Number:

| Mutant | 64 | 65 | 66 | Reference[1] |
|---|---|---|---|---|
| (Wildtype) | Phe | Ser | Tyr | Prasher et al., 1992 |
| GreenLantern-1 | Phe | Thr | Tyr | Evans et al., 1996 |
| Humanized GFP | Phe | Thr | Tyr | Zolotukhin et al., 1996 |
| Y66H | Phe | Ser | His | Heim et al., 1994 |
| Y66W | Phe | Ser | Trp |  |
| Y66F | Phe | Ser | Phe |  |
| RSGFP1 | Gly | Ser | Tyr | Delagrave et al., 1995 |
| RSGFP2 | Leu | Leu | Tyr |  |
| RSGFP3 | Gly | Cys | Tyr |  |
| RSGFP4 | Met | Gly | Tyr |  |
| RSGFP6 | Val | Ala | Tyr |  |
| RSGFP7 | Leu | Cys | Tyr |  |
| S65A | Phe | Ala | Tyr | Heim et al., 1996 |
| S65L | Phe | Leu | Tyr |  |
| S65C | Phe | Cys | Tyr |  |
| S65T | Phe | Thr | Tyr |  |
| GFPmut1 | Leu | Thr | Tyr | Cormack et al. 1996 |

[1]See preceding text for full citations.

Despite some success in overcoming certain of the above-described limitations of GFPs, the sensitivity of GFP as a reporter gene (measured as percentage of positive cells) is not as high as that of standard biochemical reporter genes such as β-gal (Evans, K., et al., *FOCUS* 18(2):40–43 (1996)). In addition, the use of GFP as a reporter gene or a protein tag requires the use of fluorescent excitation and emission optics, which increases user expense and which is more technically challenging than the use of visible or white light optics often used with standard reporters such as β-gal. Thus, a need currently exists for additional GFP variants which are more highly fluorescent, humanized, rapidly expressed in mammalian cells, capable of being observed using standard white light optics, and which provide an increased level of sensitivity.

SUMMARY OF THE INVENTION

It is thus an object of the present invention to provide mutant GFP cDNAs and proteins. In one aspect, the invention relates to such mutant GFP cDNAs which, when transfected into prokaryotic. (e.g., bacterial) or eukaryotic (e.g., mammalian) cells, increase the sensitivity of detection (measured as percentage or number of positive cells). The present invention thus provides nucleic acid molecules encoding mutant GFPs, wherein the mutant GFPs have an amino acid sequence comprising an amino acid residue lacking an aromatic ring structure at position 64 and an amino acid residue having a side chain no longer than two carbon atoms in length at position 65. Preferably, (a) if the residue at position 64 is leucine then the residue at position 65 is not cysteine or threonine; (b) if the residue at position 64 is valine then the residue at position 65 is not alanine; (c) if the residue at position 64 is methionine then the residue at position 65 is not glycine; and (d) if the residue at position 64 is glycine then the residue at position 65 is not cysteine. The invention is particularly directed to such nucleic acid molecules encoding mutant GFPs wherein the amino acid residue at position 64 is alanine, valine, leucine, isoleucine, proline, methionine, glycine, serine, threonine, cysteine, alanine, asparagine, glutamine, aspartic acid or glutamic acid, most preferably cysteine or methionine. The invention is also particularly directed to such nucleic acid molecules encoding mutant GFPs wherein the amino acid residue at position 65 is alanine, glycine, threonine, cysteine, asparagine or aspartic acid, most preferably alanine. In particular, the invention provides nucleic acid molecules encoding mutant GFPs wherein the amino acid at position 64 is cysteine or methionine and the amino acid at position 65 is alanine, and nucleic acid molecules encoding mutant GFPs having an amino acid sequence as set forth in either SEQ ID NO:5 or SEQ ID NO:6.

In additional aspects, the invention provides mutant GFPs encoded by any of the above-described nucleic acid molecules, vectors (particularly expression vectors) comprising these nucleic acid molecules, host cells (prokaryotic or eukaryotic (including mammalian)) comprising these nucleic acid molecules or vectors, and compositions comprising plasmid pGreenLantern-2/A1 or plasmid pGreenLantern-2/A4. The invention also provides methods for producing a mutant GFP, comprising culturing the above-described host cells under conditions favoring the production of a mutant GFP and isolating the mutant GFP from the host cell. The invention also provides mutant GFPs produced by these methods, particularly wherein the mutant GFPs emit fluorescent light when illuminated with white light. The invention also relates to compositions comprising the above-described mutant GFPs.

The invention is further directed to kits for transfecting a host cell with the nucleic acid molecules encoding the present mutant GFPs, such kits comprising at least one container containing a nucleic acid molecule encoding a mutant GFP such as those described above, which preferably comprises plasmid pGreenLantern-2/A1 or plasmid pGreenLantern-2/A4. These kits of the invention may optionally further comprise at least one additional container containing a reagent, preferably comprising a liposome and most preferably LIPOFECTAMINE™, for delivering a mutant GFP, nucleic acid molecule into a host cell.

The invention is further directed to kits for labeling a polypeptide with the present mutant GFPs, such kits comprising at least one container containing a mutant GFP such as those described above, preferably a mutant GFP having an amino acid sequence as set forth in SEQ ID NO:5 or SEQ ID NO:6. These kits of the invention may optionally further comprise at least one additional container containing a reagent for covalently linking this mutant GFP to the target polypeptide.

The fluorescence of all of the GFP mutants provided by the present invention is observable with fluorescein optics, making these mutant proteins amenable to use in techniques such as fluorescence microscopy and flow cytometry using standard FITC filter sets. In addition, the fluorescence of certain of the present GFP mutants, particularly those having amino acid sequences as set forth in SEQ ID NOs:5 and 6, is visible using standard white light optics (e.g., incandescent or fluorescent indoor lighting, or sunlight). The nucleic acid molecules and mutant GFPs provided by the present invention thus contribute improved tools for detection of transfection, for fluorescent labeling of proteins, for construction of fusion proteins allowing examination of intracellular protein expression, biochemistry and trafficking, and for other applications requiring the use of reporter genes.

Other preferred embodiments of the present invention will be apparent to one of ordinary skill in light of the following drawings and description of the invention, and of the claims.

BRIEF DESCRIPTION OF THE FIGURES

FIG. 1 is a depiction of the nucleotide (SEQ ID NO:1) and deduced amino acid (SEQ ID NO:2) sequences of humanized S65T mutant *A. victoria* Green Fluorescent Protein cDNA (after Zolotukhin, S., et al., *J. Virol.* 70:4646–4654 (1996)).

FIG. 2 is a depiction of the nucleotide (SEQ ID NO:3) and deduced amino acid (SEQ ID NO:4) sequences of *A. victoria* Green Fluorescent Protein cDNA (after Prasher, D. C., et al., *Gene* 111:229–233 (1992)).

FIG. 3 is a depiction of the amino acid sequence (SEQ ID NO:5) of the A1 GFP mutant.

FIG. 4 is a depiction of the amino acid sequence (SEQ ID NO:6) of the A4 GFP mutant.

DETAILED DESCRIPTION OF THE INVENTION

Overview

Figure 5:
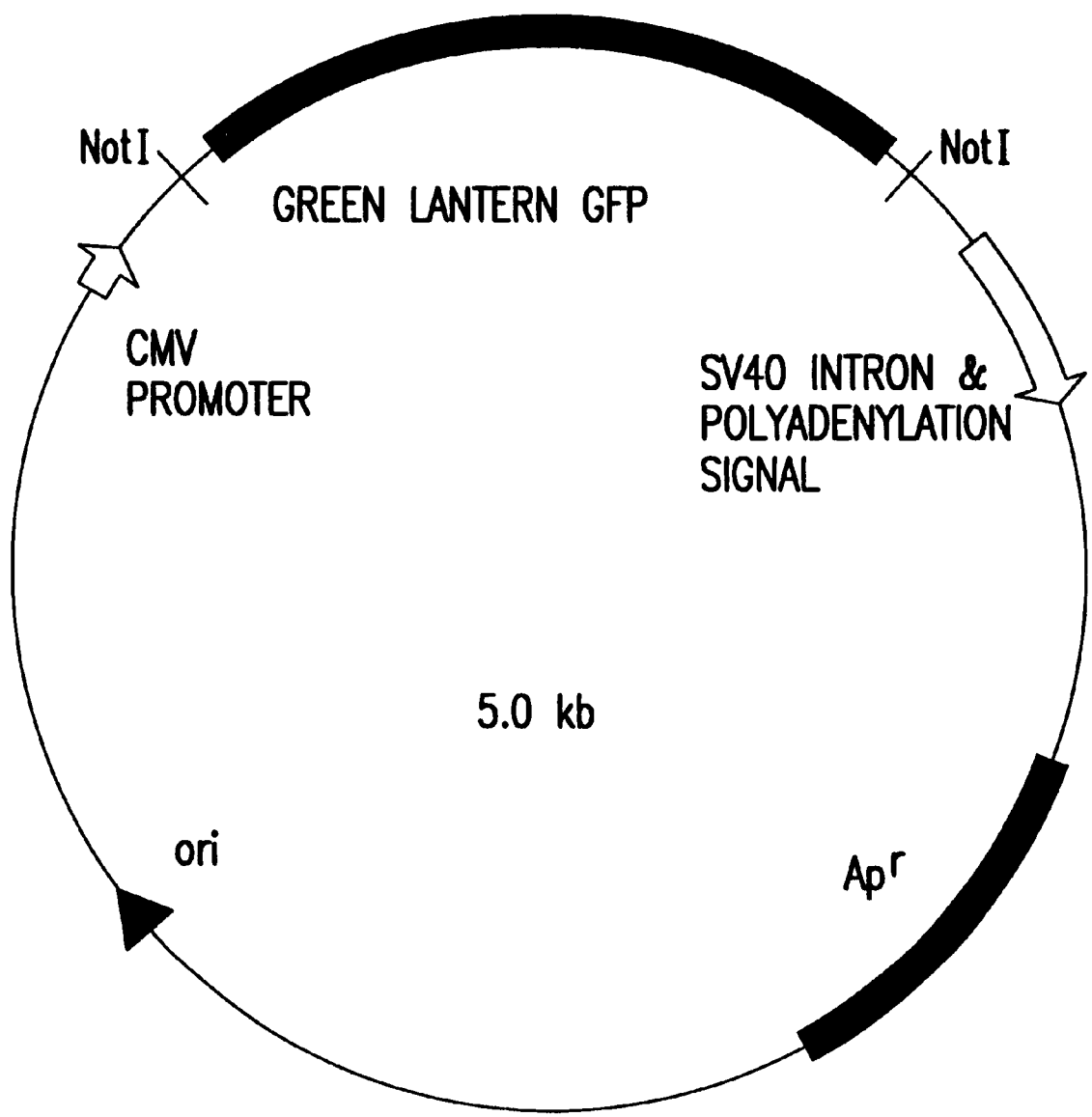
FIG. 5 is a structural map of plasmid pGreenLantern-1.

The present invention provides nucleic acid molecules encoding mutant GFPs, vectors and host cells comprising these nucleic acid molecules, the mutant GFP polypeptides, and methods for. producing mutant GFPs. Although specific plasmids, vectors, promoters, selection methods and host cells are disclosed and used herein and in the Examples, other promoters, vectors, selection methods and host cells, both prokaryotic and eukaryotic, are well-known to one of ordinary skill in the art and may be used to practice the present invention without departing from the scope of the invention or any of the embodiments thereof.

In the present invention, GFPs with selective point mutations at amino acid positions 64 and 65 have been constructed and analyzed. In general, it has been discovered in the present invention that when the amino acid residue at position 64 (phenylalanine in wt-GFP) is mutated to an amino acid lacking an aromatic ring (e.g., alanine, valine, leucine, isoleucine, proline, methionine, glycine, serine, threonine, cysteine, asparagine, glutamine, aspartic acid, glutamic acid, lysine, arginine or histidine), an increase in fluorescence quantum yield is observed. Increased fluorescence intensity is also observed when the amino acid residue at position 65 (serine in wt-GFP) is mutated to an amino acid having a side chain consisting of no more than two carbon atoms (e.g., alanine, glycine, threonine, cysteine, asparagine or aspartic acid), which induce a significant "red-shift" in excitation maximum from ultraviolet to visible blue wavelengths and a single excitation maximum instead of a dual excitation maximum as in the wildtype protein. Together, these general results indicate that in order to construct GFP mutants with a dramatic increase in fluorescence intensity from wt-GFP, either position 64 or position 65 should contain a reactive amino acid, although particular amino acids appear to be preferred at each position as described below. Furthermore, it has been unexpectedly discovered that several of the mutant GFPs of the present invention, unlike those previously known in the art, will emit fluorescence when illuminated by white light (e.g., incandescent or fluorescent indoor lighting, or sunlight).

Accordingly, in the present invention, specific mutations are introduced into positions 64 and 65 of the wt-GFP cDNA sequence (SEQ ID NO:3). Alternatively, increased expression of the present mutant GFPs may be obtained by introducing the preferred mutations into a humanized GFP gene such as that described previously (SEQ ID NO:1) (Evans, K., et al., *FOCUS* 18(2):40–43 (1996); Zolotukhin, S., et al., *J. Virol.* 70:4646–4654 (1996)).

Construction of GFP Mutants

Preparation of GFP Plasmids

The wt-GFP may be cloned from its natural source, *Aequorea victoria*, as described (Prasher, D. C., et al., *Gene* 111:229–233 (1992)). More preferably, GFP cDNA to be mutated is contained within a plasmid construct or vector, preferably an expression vector, suitable for use in transfecting mammalian cells, such as pRAY-1 wherein the wt-GFP cDNA is under the control of the human cytomegalovirus (CMV) enhancer/promoter (Marshall, J., et al., *Neuron* 14:211–215 (1995)). Most preferably, to provide for optimum expression of the mutant GFPs in mammalian cells, the humanized S65T mutant GFP cDNA (Evans, K., et al., *FOCUS* 18(2):40–43 (1996); Zolotukhin, S., et al., *J. Virol.* 70:4646–4654 (1996)) under control of the CMV enhancer/promoter may be used, contained in plasmid pGreenLantern-1 (FIG. 5), which is available commercially from Life Technologies, Inc. (Rockville, Md.).

The above-described plasmids may be used directly for preparation of mutant GFP cDNAs according to the present invention. Alternatively, a stop codon in the 5' multiple cloning site of pGreenLantern-1 may be shifted out of frame by oligonucleotide ligation methods to allow the mutant GFPs of the present invention to be used in the construction of fusions between GFP and other proteins, as described below.

Mutations to GFP cDNA

A variety of random or site-directed mutagenic techniques may be used to prepare the mutant GFPs of the present invention. Appropriate methods include chemical mutagenesis using, for example, sodium bisulfite or hydroxylamine (Myers, R. M., et al., *Science* 229:242–247 (1985); Sikorski, R. S., and Boeke, J. D., *Meth. Enzymol.* 194:302–318 (1991)), linker insertion mutagenesis (Heffron, F., et al., *Proc. Natl. Acad Sci. USA* 75:6012–6016 (1978)), deletion mutagenesis (Lai, C. J., and Nathans, D., *J. Mol. Biol.* 89:179–193 (1974); McKnight, S. L., and Kingsbury, R., *Science* 217:316–324 (1982)), enzyme misincorporation mutagenesis (Shortle, D., et al., *Proc. Natl. Acad. Sci. USA* 79:1588–1592 (1982)), oligonucleotide-directed mutagenesis (Hutchinson, C. A., et al., *J. Biol. Chem.* 253:6551–6560 (1978); Zoller, M. J., and Smith, M., *Nucl. Acids Res.* 10:6487–6500 (1982); Taylor, J. W., et al., *Nucl. Acids Res.* 13:8765–8785 (1985)), and cassette mutagenesis (Lo, K. -M., et al., *Proc. Natl. Acad. Sci. USA* 81:2285–2289 (1984); Wells, J. A., et al., *Gene* 34:315–323 (1985)). To improve the fidelity and efficiency of mutagenesis, the use of the polymerase chain reaction (PCR) in accomplishing GFP mutagenesis by one or more of the foregoing methods is preferred (Higuchi, R., et al., *Nucl. Acids Res.* 16:7351–7367 (1988);

Leung, D. W., et al., *Technique* 1:11–15 (1989); Clackson, T., and Winter, G., *Nucl. Acids Res.* 17:10163–10170 (1989)).

Most preferably, mutations are made to GFP cDNA by uracil DNA glycosylase (UDG) mutagenesis using PCR amplification (Nisson, P., et al., *PCR Meth. Appl.* 1:120–123 (1991)). In this approach, the plasmid containing GFP cDNA, most preferably pGreenLantern-1 comprising humanized S65T GFP (FIG. 5), is used as the PCR template, and a sense or antisense primer consisting essentially of an oligonucleotide containing at least one mismatched nucleotide (available commercially from Life Technologies, Inc.; Rockville, Md.) is added to the reaction mixture. Amplification reaction mixtures most preferably contain 1× PCR buffer, about 10 micromolar each of deoxyATP, deoxyTTP, deoxyCTP and deoxyGTP, about 25 picomoles each of sense and antisense primers and about 10 nanograms of template. PCR is performed by techniques that are routine in the art, and after at least five PCR cycles, samples of the reaction mixture are treated with UDG, most preferably for 30 minutes at 37° C., as described (Nisson, P., et al., *PCR Meth. Appl.* 1:120–123 (1991)).

The mutated GFP nucleic acid molecules preferably will comprise nucleic acid sequences encoding mutant proteins in which one or more amino acid residues have been mutated from the wildtype amino acid sequence set forth in FIG. 2 and SEQ ID NO:4. Such mutations may include, for example, substitutions, deletions, insertions or modifications, and preferably are amino acid substitutions. Particularly preferred are amino acid substitutions occurring in the three amino acid chromophore of GFP at residues 64, 65 and 66 of the wildtype GFP sequence (FIG. 2 and SEQ ID NO:4), wherein the phenylalanine residue at position 64 (Phe64), the serine residue at position 65 (Ser65), and the tyrosine residue at position 66 (Tyr66), are each individually, or all together, replaced by other amino acid residues. More preferred mutant GFPs of the invention include, but are not limited to, those with the following substitutions from the wildtype GFP sequence shown in FIG. 2 and SEQ ID NO:4:

serine 65 replaced by threonine (Ser65→Thr);
Phe64→Cys and Ser65→Ala (SEQ ID NO:5);
Phe64→Cys and Ser65→Thr;
Phe64→Leu and Ser65→Thr;
Phe64→Met and Ser65→Ala (SEQ ID NO:6);
Phe64→Met and Ser65→Thr;
Phe64→Met, Ser65→Phe and Tyr66→Phe;
Phe64→Met, Ser65→Phe and Tyr66→Lys;
Phe64→Thr and Ser65→Cys; and
Phe64→Val and Ser65→Cys Other suitable mutations and mutant GFP amino acid sequences may be determined by one of ordinary skill without undue experimentation according to the methods described herein and others that are known in the art. As a practical matter, whether a particular mutation or combination of mutations produces a mutant GFP that may have the above-described desirable properties (e.g., higher expression in mammalian cells, higher fluorescence intensity under UV or white light illumination) may be determined by one of ordinary skill using the mutation, transfection, expression and detection methods described in detail below in the Examples, as well as using standard techniques that are routine in the art.

Figure 6:
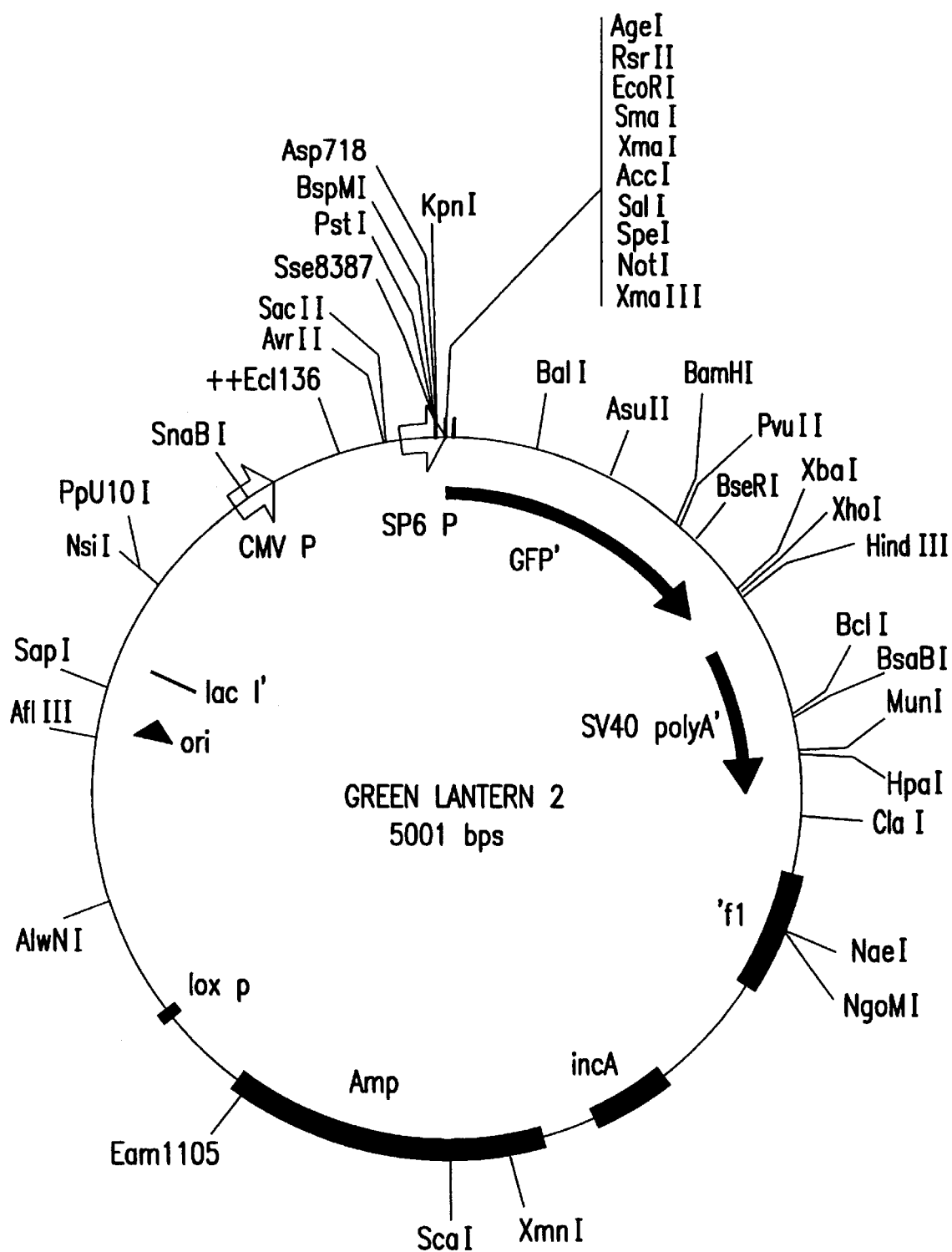
FIG. 6 is a structural map of plasmid pGreenLantern-2.

Following mutagenesis by any of the above-described methods, the resulting nucleic acid molecules encoding the mutant GFPs may be inserted into one or more vectors, such as those described above, which are preferably expression vectors. A particularly preferred vector for containing the present mutant GFP nucleic acid molecules is p-GreenLantern-2 (FIG. 6). Methods for producing the mutant GFP-vector constructs will be familiar to those of ordinary skill, and are provided in detail below in Example 1.

Once they have been constructed, the vectors comprising the mutant GFP nucleic acid molecules may be formulated into a variety of compositions, such as solutions (e.g., buffer solutions) to be used in transfecting host cells, Alternatively, the vector constructs may be purified and stored according to standard techniques for handling recombinant DNA plasmid vectors (Sambrook, J., et al., *Molecular Cloning, a Laboratory Manual,* 2nd Ed., Cold Spring Harbor, N.Y.: Cold Spring Harbor Laboratory Press, pp. 1.3–1.20 (1989)).

More preferably, the mutant GFP-containing plasmid vectors are transformed into a competent host cell. Any competent host cell may be used, including those of bacteria (e.g., *E. coli*), yeast (e.g., *Saccharomyces* spp.), insects (e.g., *Spodoptera* spp.) and mammals (e.g., CHO or BHK cells), although a competent strain of *E. coli* such as DH10B (Life Technologies, Inc.; Rockville, Md.) is most preferably used. Transformation of mutagenized GFP cDNAs into host cells may be accomplished by any technique generally used for introduction of exogenous DNA, including the chemical, viral, electroporation, lipofection and microinjection methods that are well-known in the art. Particularly preferred methods for transformation includ electroporation and liposome-mediated transfection (lipofection), the latter most preferably being accomplished using LIPOFECTAMINE™ (Life Technologies, Inc.; Rockville, Md.).

After expansion of transformed cultures, mutated GFP cDNA is isolated from the host cells by routine methods (Sambrook, J., et al., *Molecular Cloning, a Laboratory Manual,* 2nd Ed., Cold Spring Harbor, N.Y.: Cold Spring Harbor Laboratory Press, pp. 1.21–1.52 (1989)) and is subcloned into a plasmid backbone for use in subsequent transfections. Most preferably, this plasmid backbone is the pGreenLantern-2 backbone (see FIG. 6) which contains a universal sequencing primer downstream from a CMV enhancer promoter and an NsiI site immediately upstream of the CMV promoter allowing excision of the promoter region, along with XbaI, XhoI and HindIII sites in place of the 3' NotI site in pGreenLantern-1 (FIG. 4).

Fusion sequences of GFP cDNA with nucleotide sequences encoding proteins of interest may be prepared by cloning the desired sequence(s) into pGreenLantern-2 at the 5' multiple cloning site using standard techniques. These fusion constructs allow the use of the mutant GFPs of the present invention as reporters of transfection efficiency. In addition, fusion constructs such as these will allow a direct examination of the expression, biochemistry and localization of the fused proteins intracellularly.

Alternatively, to examine the structure and function of regulatory sequences (e.g., promoters, enhancers, inhibitors) in native genes, the GFP mutant cDNAs may be directly transfected or inserted, using routine methods, into target genomic or extrachromosomal DNA sequences in host cells (Chalfie, M., et al., *Science* 263:802–805 (1994)).

Transfection of Hosts With GFP Mutants

Target cells to be transfected with cDNAs comprising mutant GFPs (either fused or unfused to accessory sequences) are grown and maintained in culture according to routine methods. Cells may be transfected with mutant GFP cDNA by any method described above, although electroporation or liposome-mediated transfection (particularly using LIPOFECTAMINE™) are preferred. Following transfection, cells are incubated for 12–48 hours, preferably 18–24 hours and most preferably for about 24 hours. Transfected cells may then be examined for the expression of mutant GFP, manifested as green intracellular fluorescence. With standard optical filters routinely used for examining fluorescein (typically excitation wavelength of about 475 nm, dichroic filter of 485 nm, emission wavelength of about 490 nm), this fluorescence may be examined qualitatively, for example by fluorescence microscopy, or quantitatively, for example by spectrofluorimetry or flow cytofluorimetry. In addition, transfected cells expressing relatively high amounts of mutant GFPs of the present invention may be separated from non-transfected cells, or from those expressing lower levels of GFP, by fluorescence-based single cell separation techniques such as fluorescence-activated cell sorting. Alternatively, transfected cells expressing mutant GFPs that fluoresce under white light illumination, particularly those having amino acid sequences as set forth in SEQ ID NOs: 5 and 6, may be examined by the above-described qualitative and quantitative methods using standard white light optics (e.g., incandescent or halogen lighting, or sunlight).

These transfected host cells may also be used in methods for the production of mutant GFPs of the invention. Such methods may comprise, for example, culturing the above-described host cells under conditions favoring the production of the mutant GFPs by the host cells, and isolating the mutant GFPs from the host cells and/or the culture medium in which the host cells are cultured. Typical host cell culture conditions favoring production of recombinant proteins, such as the present mutant GFPs, are well-known in the art (see, e.g., Sambrook, J., et al., *Molecular Cloning, a Laboratory Manual,* 2nd Ed., Cold Spring Harbor, N.Y.: Cold Spring Harbor Laboratory Press (1989)). The mutant GFPs produced by these methods may then be isolated by any of a number of protein purification techniques, such as chromatography (preferably affinity chromatography, HPLC or FPLC), salt extraction (such as ammonium sulfate precipitation), electrophoresis, dialysis, or a combination thereof, to produce isolated mutant GFPs of the invention. These mutant GFPs may then be stored until use (preferably at temperatures below 0° C., more preferably at about –20 C. to about –70° C.), or they may be formulated into compositions. Preferred such compositions may comprise, for example, one or more of the mutant GFPs of the invention and one or more additional components, such as one or more buffer salts, one or more inorganic salts or ions thereof, one or more detergents, one or more preservatives, and the like, preferably in an aqueous or organic solvent.

Detection Methods

In additional embodiments, the invention relates to methods of detecting the presence of a mutant GFP, or of a cell (such as a prokaryotic or eukaryotic, including mammalian, cell) expressing a mutant GFP. Such methods of the invention may comprise, for example, illuminating the mutant GFP or cell expressing the mutant GFP with a source of white light under conditions such that the mutant GFP or cell expressing the mutant GFP emits visible fluorescent light. In the present methods, the illumination source may be any light source emitting white (ie., visible) light, including but not limited to an incandescent light source, a fluorescent light source, a halogen light source, sunlight, and the like. When illuminated by such a white light source, mutant GFPs, such as those of the present invention, will emit fluorescent light of various visible wavelengths (depending upon the specific mutations contained in the mutant GFP, as described above), which may be detected by eye or by any of the above-described qualitative or quantitative mechanical means.

Kits

In other preferred embodiments, the compositions of the present invention may be assembled into kits for use in transfecting host cells with the nucleic acid molecules encoding the present mutant GFPs, or for labeling target polypeptides with the present mutant GFPs. Host cell transfection kits according to the present invention may comprise at least one container containing one or more of the above-described nucleic acid molecules encoding a mutant GFP (or a composition comprising one or more of the nucleic acid molecules or plasmids described above), which nucleic acid molecule preferably comprises plasmid pGreenLantern-2/A1or plasmid pGreenLantern-2/A4 (see Example 1 below). These transfection kits of the invention may optionally further comprise at least one additional container which may contain, for example, a reagent for delivering the mutant GFP nucleic acid molecule into a host cell; in preferred kits, this reagent may comprise a liposome and most preferably LIPOFECTAMINE™. Polypeptide labeling kits according to the present invention may comprise at least one container containing, for example, a mutant GFP such as those described above (or a composition of the invention comprising a mutant GFP), which is preferably a mutant GFP having an amino acid sequence as set forth in SEQ ID NO:5 or SEQ ID NO:6. These labeling kits of the invention may optionally further comprise at least one additional container which may contain, for example, a reagent for covalently linking the mutant GFP to the target polypeptide.

Use of Mutant GFPs

The mutant GFPs and kits of the present invention may be used in a variety of applications. For example, the mutant GFP cDNAs are useful as reporter genes that allow a determination of transfection efficiency and success (Chalfie, M., et al., *Science* 263:802–805 (1994)). Alternatively, the mutant proteins themselves may be used as fluorescent labels suitable for detectably labeling other proteins, nucleic acids or particulates to be used in a variety of applications (Heim, R., et al., *Proc. Natl. Acad. Sci. USA* 91:12501–12504 (1994); Yokoe, H., and Meyer, T., *Nature Biotech.* 14:1252–1256 (1996)), such as labeling antibodies used in infectious disease diagnostic methods; mutant GFPs may be attached to target polypeptides and proteins by a variety of methods that are well-known to one of ordinary skill in the art, including the use of chemical coupling reagents. In addition, fusion complexes between GFP and other proteins may be constructed to allow closer and more sensitive determinations of the expression, biochemistry, localization and trafficking of intracellular proteins in many host cells (Heim, R., et al., *Proc. Natl. Acad. Sci. USA* 91:12501–12504 (1994); Wang, S., and Tulle, H., *Nature* 369:400–403 (1994); Marshall, J., et al., *Neuron* 14:211–215 (1995); Rizzuto, R, et al., *Curr. Biol.* 6:183–188 (1996)). Importantly, use of the mutant GFPs that emit fluorescence when illuminated by white light will spare the user considerable expense and technical difficulty that can accompany the use of fluorescent optics for the examination of fluorescent reporter genes such as GFP.

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Example 1

Construction of Mutant GFP cDNAs

Plasmids

As depicted in FIG. 5, pGreenLantern-1 (Life Technologies, Inc., Rockville, Md.; catalogue no.10642) contains the humanized S65T mutant GFP cDNA (FIG. 1; SEQ ID NOs: 1, 2) (Evans, K., et al., *FOCUS* 18(2):40–43 (1996); Zolotukhin, S., et al., *J. Virol.* 70:4646–4654 (1996)). This plasmid serves as the source of the GFP DNA sequence used for mutagenesis. As depicted in FIG. 6, pGreenLantern-2 contains a universal sequencing primer downstream of the CMV promoter along with an NsiI site immediately upstream of the CMV promoter allowing excision of the promoter region. It also contains XbaI, XhoI and HindIII sites in place of the 3' NotI site in pGreenLantern-1. A stop codon in the 5' multiple cloning site of pGreenLantern-1 was shifted out of frame to allow possible fusions to GFP in pGreenLantern-2.

Mutations to GFP CDNA by UDG Cloning.

PCR was performed in an MJ Research DNA Engine™ thermal cycler using the following conditions: 94° C. for 60 seconds, 94° C. for 30 seconds, 55° C. for 30 seconds and 72° C. for 4 minutes, repeated for 20 cycles. Sense oligonucleotide primers containing specific mismatches to the wt-GFP sequence (SEQ ID NOs:7–15; Table 2) were obtained from Life Technologies, Inc. (Rockville, Md.).

TABLE 2

Sense Oligonucleotides Used for UDG Cloning Mutations.

| Vector | Amino Acid Mutations | Single-stranded Oligonucleotide Sequence (5' to 3') | SEQ ID NO: |
|---|---|---|---|
| pGreen-Lantern-2/A1 | Cys64, Ala65 | CAACACUGGUCACUACCTG-CGCCTATGGCGTGC | 7 |
| pGreen-Lantern-2/A2 | Cys64, Thr65 | CCAACACUGGUCACUACCT-GCACCTATGG | 8 |
| pGreen-Lantern-2/A3 | Leu64, Thr65 | CAACACUGGUCACUACCCT-CACCTATGGCGTGCAGT | 9 |
| pGreen-Lantern-2/A4 | Met64, Ala65 | CAACACUGGUCACUACAAT-GGCCTATGGCGTGCAGTGCT | 10 |
| pGreen-Lantern-2/A5 | Met64, Thr65 | CAACACUGGUCACUACCAT-GACCTATGGCGTGCAGTGCT | 11 |
| pGreen-Lantern-2/A6 | Met64, Phe65, Phe66 | CAACACUGGUCACUACCAT-GTTCTTCGGCGTGCAGTGCT | 12 |
| pGreen-Lantern-2/A7 | Met64, Phe65, Lys66 | CAACACUGGUCACUACCAT-GTTCAAGGGCGTGCAGTGCT | 13 |
| pGreen-Lantern-2/A8 | Thr64, Cys65 | CAACACUGGUCACUACCAC-ATGCTATGGCGTGCAGT | 14 |
| pGreen-Lantern-2/A9 | Val64, Cys65 | CAACACUGGUCACUACCGT-GTGCTATGGCGTGCAGT | 15 |

The antisense oligonucleotide primer used for each mutation set had the following sequence: 5'-AGU-GAC-CAG-UGU-UGG-CCA-AGG-CAC-AGG-GAG-CTT-3' (SEQ ID NO:16). The template plasmid used was pGreenLantern-1 (FIG. 5) with a universal reverse sequencing primer incorporated into the backbone. Amplifications reactions contained 1X PCR buffer, 10 micromolar deoxynucleoside triphosphates, 25 picomoles of each primer (sense and antisense) and 10 nanograms of template DNA in a 50 microliter volume. After 6, 9 and 20 PCR cycles were completed, 10 microliter samples were taken and checked via agarose gel electrophoresis for excess background. Two 20 microliter samples of each 6-cycle aliquot were digested with DpnI at 37° C. for 30 minutes, then at 75° C. for 15 minutes and allowed to cool to room temperature. One of the samples from each reaction (four samples in all) was treated with one unit of uracil DNA glycosylase (UDG) at 37° C. for 30 minutes (Nisson, P., et al., *PCR Meth. Appl.* 1:120–123 (1991)). PCR samples were then transformed into 100 microliters of MAX Efficiency DH10B™ Competent Cells (Life Technologies, Inc.; Rockville, Md.). The mutated portion of the GFP cDNA was then subcloned with a NotI and BamHI digest into the pGreenLantern-2 backbone (FIG. 6) which was not subjected to PCR (Sambrook, J., et al., *Molecular Cloning, a Laboratory Manual,* 2nd Ed., Cold Spring Harbor, N.Y.: Cold Spring Harbor Laboratory Press (1989)). This approach yielded nine separate mutant GFP plasmid vectors, designated pGreenLantern-2/A1 through pGreenLantern-2/A9 (Table 2), each with a specific mutation or set of mutations within the GFP chromophore region at amino acids 64–66.

Example 2

Growth and Transfection of Host Cells with Mutant GFPs

Cell Culture

Chinese hamster ovary cells (CHO-K1, obtained from American Type Culture Collection (ATCC), Rockville, Md.) were cultured in D-MEM (4,500 milligrams/liter D-glucose with L-glutamine and phenol red) plus 10% fetal bovine serum (FBS), 0.1 millimolar nonessential amino acids, 2.5 units per milliliter penicillin and 2.5 micrograms per milliliter streptomycin (Freshney, R. I., *Culture of Animal Cells: A Manual of Basic Techniques,* 3rd Ed., New York: Wiley-Liss (1994)). Cells were grown at 37° C. in a 5% $CO_2$/air incubator. All media and reagents were from Life Technologies, Inc., Rockville, Md.

Transfection

CHO-K1 cells were plated at $2 \times 10^5$ cells per well into six-well (35 millimeter diameter) plates one day prior to transfection. Immediately before transfection, cells were rinsed with medium containing no serum or antibiotics. LIPOFECTAMINE™ reagent was diluted into 100 microliters of OPTI-MEM-I Reduced Serum Medium (without FBS) to give a final concentration of LIPOFECTAMINE of 6 microliters per well. DNA was diluted separately to a concentration of 1 microgram per well in 100 microliters of OPTI-MEM-I. Transfection complexes were formed by combining diluted lipid and DNA and incubating for 30 minutes prior to addition to cells. Transfection complexes were then diluted 1:5 with D-MEM containing no FBS or antibiotics and added to the rinsed cells. Cells were transfected for five hours at 37° C., then fed with an equal volume of D-MEM containing 20% FBS, 0.1 millimolar nonessential amino acids, and no antibiotics. Cells were grown overnight at 37° C., 5% $CO_2$/air. In some studies, cells were grown for 48 hours; in these studies, transfection complexes were removed from cells 24 hours after addition and cells were fed with 2 milliliters per well of complete medium.

Regardless of the vector used, host cells transfected with the mutant GFP genes demonstrated approximately equivalent growth rates as control cells transfected with the wild-type GFP gene or with other reporter genes (e.g., β-gal).

These results indicate that transfection with the mutant GFP cDNAs of the present invention does not adversely affect the growth or culturability of the host cells more than transfection with any other reporter vector.

Example 3

Characterization of GFP Mutants Expressed in Eukaryotic Cells

Formalin Fixation

Transfected host cells were rinsed in Dulbecco's Phosphate Buffered Saline (PBS), then fixed in a solution of 10% formalin in PBS for one hour. Formalin was then removed, and cells were rinsed and stored in PBS at 4° C. until being analyzed.

Fluorescence Microscopy

Formalin-fixed cells were examined and photographed using an inverted phase contrast fluorescence microscope equipped with FITC filters (excitation 475 nm/dichroic 485 nm/barrier 490 nm) and a 50 watt mercury arc bulb at 1.25 volts. A 40×-power adjustable non-phase objective was used for all micrographs, which were taken through blue, neutral and FITC filters using Kodak Ektachrome ASA 400 Daylight (for slides) or Kodak Gold ASA 400 Daylight (for prints). All exposures were for 12 seconds to allow unbiased comparison of fluorescence intensity.

Flow Cytofluorimetry

Flow cytofluorimetry was performed on transfected CHO-K1 cells that were trypsinized and suspended in PBS plus 10% formalin at a concentration of less than $10^6$ cells per milliliter. Measurements were made on a Coulter EPICS®XL-MCL flow cytometer using a 15 megawatt argon ion laser. Filters used were 488 nm excitation, 500 nm dichroic LP/525 nm band pass for FL1 (green channel) and 575 band pass/600 nm dichroic LP for FL2 (orange channel). Samples consisted of 20,000 events using PMT voltages of 100 volts for side scatter and forward scatter, 496 volts for FL1 and 505 volts for FL2, all with integral gain set to 1.0. Color compensation included 7.9% orange signal in FL1 and 3.2% green signal in FL2.

Results

Figure 7:
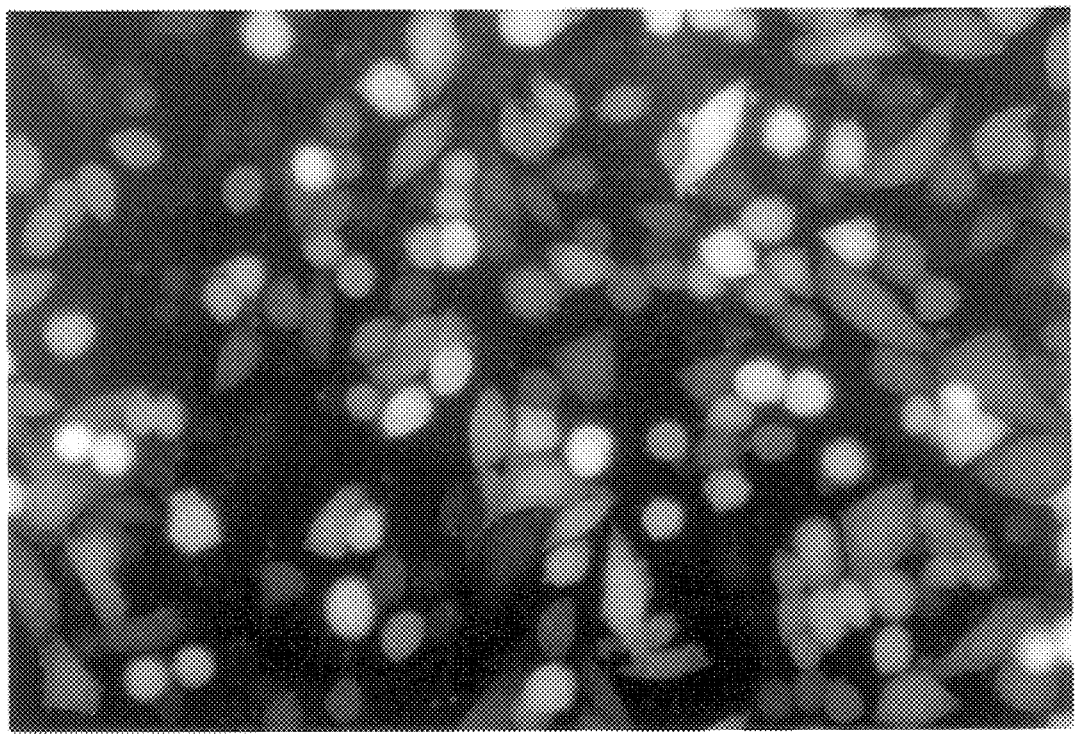
FIG. 7 is a fluorescence photomicrograph of CHO-K1 cells viewed 24 hours after transfection with the A1 GFP mutant (plasmid pGreenLantern-2/A1).
Figure 8:
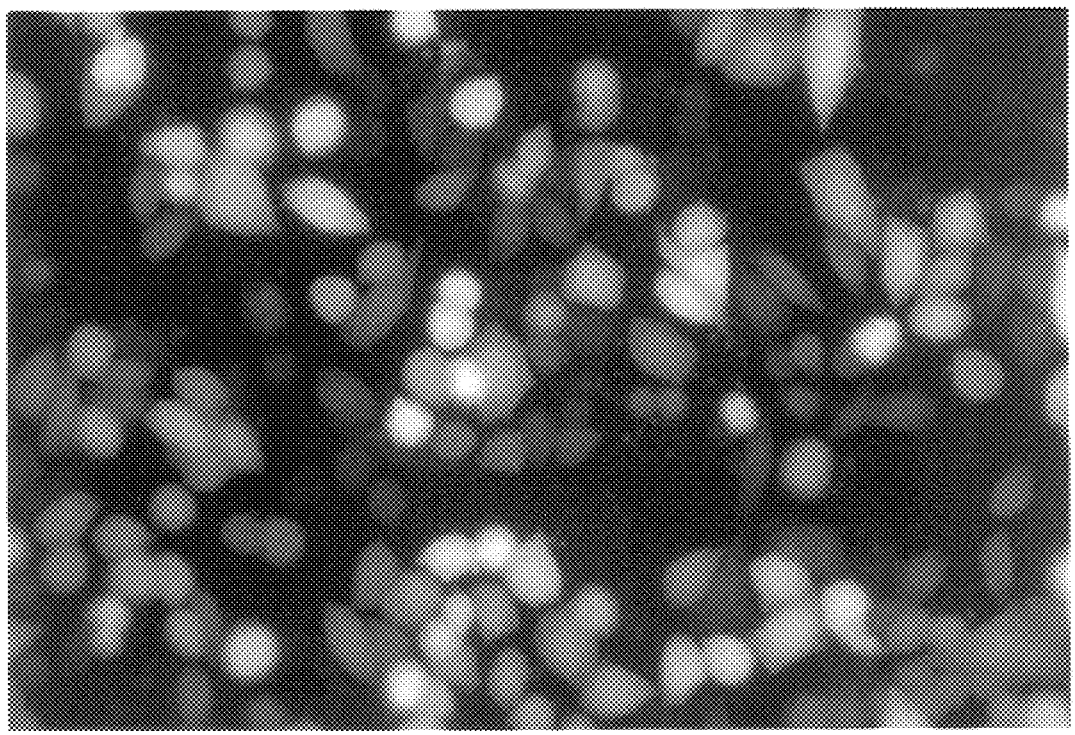
FIG. 8 is a fluorescence photomicrograph of CHO-K1 cells viewed 24 hours after transfection with the A4 GFP mutant (plasmid pGreenLantern-2/A4).
Figure 9:
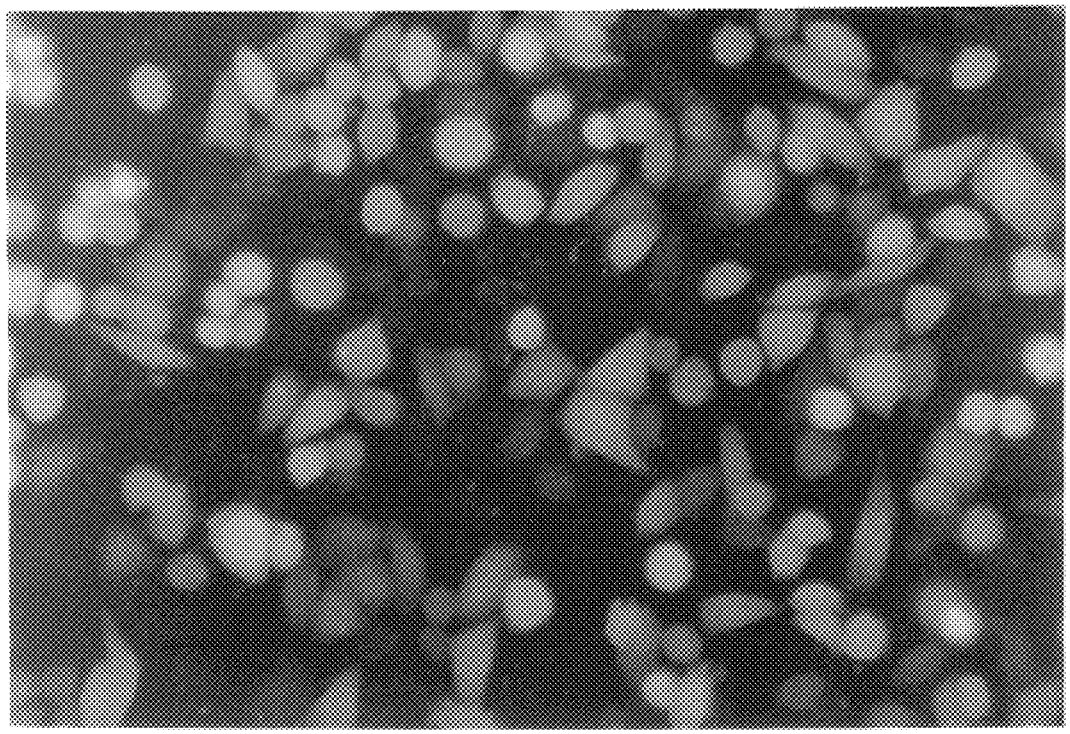
FIG. 9 is a fluorescence photomicrograph of negative control CHO-K1 cells viewed 24 hours after transfection with the pGreenLantern-2 backbone.

As shown in Table 3, the GFP mutants of the present invention displayed varying intensities and kinetics of formation in transfected cells. Two of these mutants, designated "A1" (phenylalanine mutated to cysteine at position 64; serine mutated to alanine at position 65; FIG. 3; SEQ ID NO:5) and "A4" (phenylalanine mutated to methionine at position 64; serine mutated to alanine at position 65; FIG. 4; SEQ ID NO:6) were exceptionally bright. As shown in FIGS. 7–9, CHO cells transfected with plasmid pGreenLantern-2/A1 (FIG. 7) or with plasmid pGreenLantern-2/A4 (FIG. 8) demonstrated a dramatic increase in green fluorescence intensity over cells transfected with the humanized S65T mutation of pGreenLantern-1 (FIG. 9) when viewed at 24 hours post-transfection using FITC optics.

TABLE 3

Effects of Point Mutations on GFP Fluorescence Intensity.

| Vector | Amino Acids | Fluorescence Results |
|---|---|---|
| Wildtype GFP | Phe64, Ser65 | $\lambda_{ex}$ = 395 nm (major), 470 nm (minor); 48 hours required for detection |
| S65T | Phe64, Thr65 | 6-fold increase in intensity over wildtype |
| pGreenLantern-1 | Phe64, Thr65 (humanized) | 22-fold increase in intensity over wildtype |
| pGreenLantern-2/A1 | Cys64, Ala65 | 6-fold increase in intensity over S65T |
| pGreenLantern-2/A2 | Cys64, Thr65 | 22-fold increase in intensity over wildtype |
| pGreenLantern-2/A3 | Leu64, Thr65 | 6-fold increase in intensity over S65T |
| pGreenLantern-2/A4 | Met64, Ala65 | 6-fold increase in intensity over S65T |
| pGreenLantern-2/A5 | Met64, Thr65 | Slight increase in intensity over pGreenLantern-1 |
| pGreenLantern-2/A6 | Met64, Phe65, Phe66 | Equivalent to wildtype |
| pGreenLantern-2/A7 | Met64, Phe65, Lys66 | Equivalent to wildtype |
| pGreenLantern-2/A8 | Thr64, Cys65 | Equivalent to wildtype |
| pGreenLantern-2/A9 | Val64, Cys65 | Slight increase in intensity over pGreenLantern-1 |

Other mutants produced in the present studies were less satisfactory (Table 3). For example, mutants A5 (phenylalanine mutated to methionine at position 64; serine mutated to threonine at position 65) and A9 (phenylalanine mutated to valine at position 64; serine mutated to cysteine at position 65) gave only slightly better fluorescence than the humanized S65T mutation of pGreenLantern-1. It is possible that the highly reactive cysteine at position 65 in mutant A9 may interfere with the formation of the three amino acid heterocyclic ring required for GFP fluorescence (Cody, C. W., *Biochemistry* 32:1212–1218 (1993)).

Mutant A2 (phenylalanine mutated to cysteine at position 64; serine mutated to threonine at position 65) was equal in fluorescence to the humanized S65T pGreenLantern-1 (Evans, K., et al., *FOCUS* 18(2):40–43 (1996); Zolotukhin, S., et al., *J. Virol.* 70:4646–4654 (1996)), while mutants A6 (phenylalanine mutated to methionine at position 64; serine mutated to phenylalanine at position 65; tyrosine mutated to phenylalanine at position 66), A7 (phenylalanine mutated to methionine at position 64; serine mutated to phenylalanine at position 65; tyrosine mutated to lysine at position 66) and A8 (phenylalanine mutated to threonine at position 64; serine mutated to cysteine at position 65) demonstrated a decreased fluorescence intensity and were, in fact, equivalent to wt-GFP. No shift in excitation or emission spectra was detected with these three mutants, however, as no fluorescence was observed using ultraviolet or rhodamine filter combinations.

Figure 10:
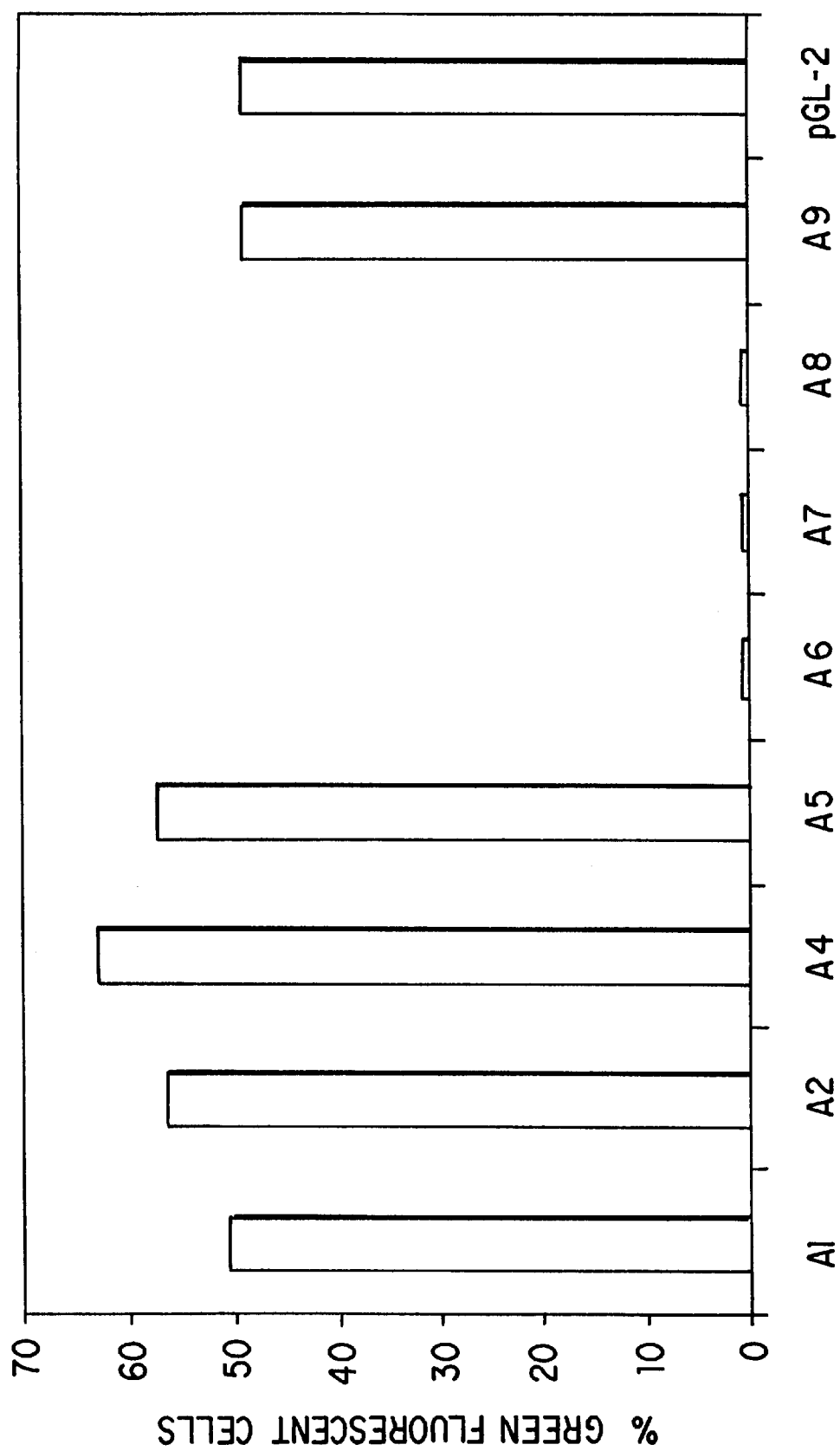
FIG. 10 is a bar graph demonstrating the fluorescence of CHO-K1 cells determined by flow cytometry 24 hours after transfection with various GFP mutants.
Figure 11:
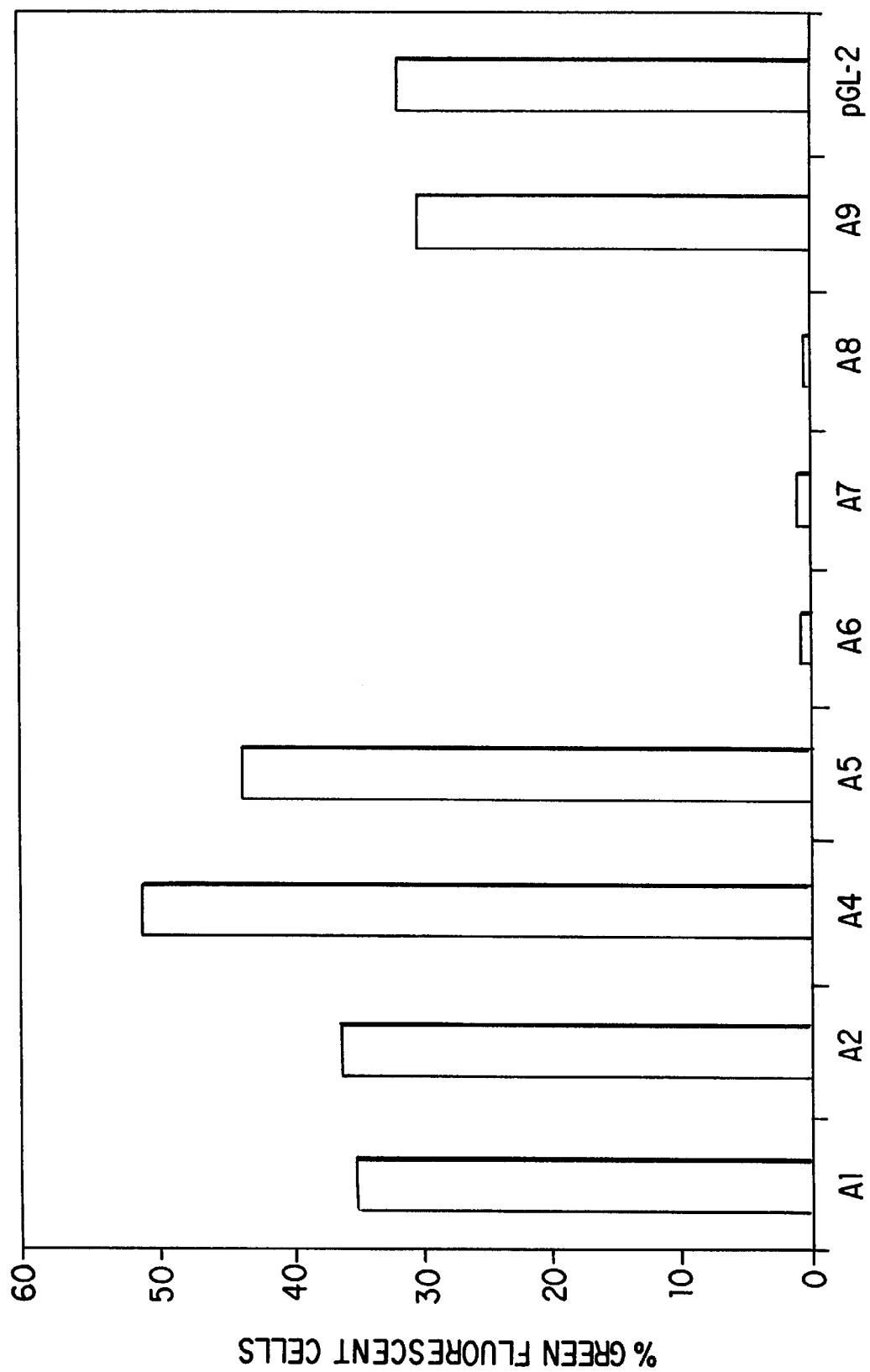
FIG. 11 is a bar graph demonstrating the fluorescence of CHO-K 1 cells determined by flow cytometry 48 hours after transfection with various GFP mutants.

These results were also observed via flow cytometry. As shown in FIG. 10, CHO-K1 cells transfected with the A1 and A4 mutant GFPs demonstrated a dramatic increase in fluorescence over wildtype and A6–A8 mutants within 24 hours of transfection. This high level of fluorescence was maintained, particularly for cells transfected with the A4 mutant GFP, for at least 48 hours after transfection (FIG. 11).

Mutations at certain amino acid positions outside the chromophore were also examined for their effects on GFP fluorescence. Mutation of Gln69→Asn in the A4 mutant resulted in a dramatic decrease in fluorescence relative to the A4 mutant itself as did mutation of Val163→Ala and Ile167→Thr in the A4 mutant.

Together, these results indicate that the most preferable mutations for providing highly fluorescent, rapidly expressed GFPs are those in which only one reactive amino acid is present at either position 64 or 65, as in the A1 (Phe64→Cys; Ser65→Ala; SEQ ID NO:5) and A4 (Phe64→Met; Ser65→Ala; SEQ ID NO:6) mutants.

Example 4

Characterization of GFP Mutants Expressed in Prokaryotic Cells

Figure 12:
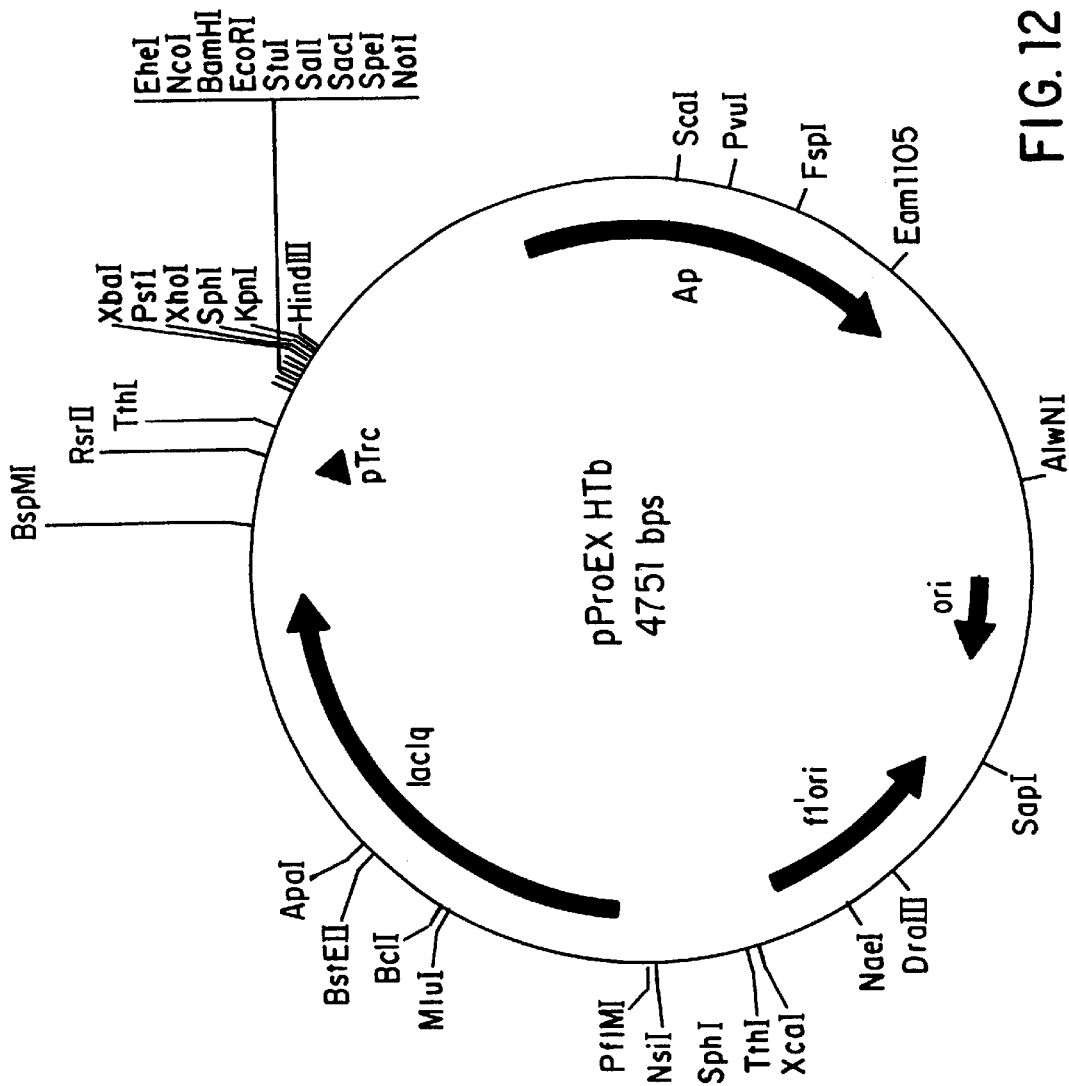
FIG. 12 is a structural map of plasmid pProEX HTb.

To examine the efficacy of expressing mutant GFPs in prokaryotic cells, mutant GFP cDNAs were subcloned into the bacterial pProEX HTb vector (FIG. 12). GFP cDNA was excised by NotI and XbaI digestion from pGreenLantern-2 (FIG. 6) containing the mutations at positions 64, 65 and/or 66 (mutants A1 through A9) shown in Table 3. The bacterial vector pProEX HTb (FIG. 12) was also digested with the same enzymes. The pProEX HTb backbone and GFP fragments were ligated, to form the corresponding transfection vectors containing the respective mutant GFP fragments: pProEXA1, pProEXA2, pProEXA3, pProEXA4, pProEXA5, pProEXA6, pProEXA7, pProEXA8 and pProEXA9. These vectors were then individually transformed into 100 μl of DH10B *E. coli* host cells; control cells were also prepared that had been transfected with a construct containing the S65T mutant described in Examples 1–3 above. Cells were plated onto ampicillin/IPTG plates and incubated overnight at 37° C., and colonies were then picked and screened for fluorescence under long ultraviolet (UV) or blue illumination.

Colonies containing the A1, A2, A3, A4, A5, A9 and S65T mutant GFPs all demonstrated green fluorescence when illuminated with long UV or blue light, while those containing the A6, A7 and A8 mutant GFPs demonstrated no fluorescence under these conditions. These results are consistent with those observed in eukaryotic cells, as shown in Example 3 above, and indicate that mutant GFPs may be successfully transfected into and expressed in prokaryotic cells.

Example 5

Visible Light Excitation of GFP Mutants

To examine the ability of mutant GFPs to emit fluorescence when illuminated by white light, *E. coli* cells were transfected and plated as described above in Example 4. Colonies were then picked and examined for fluorescence upon illumination by incandescent light, fluorescent indoor lighting, or sunlight.

Upon induction of the host cells with IPTG, cells transformed with the vector comprising the A4 GFP mutation unexpectedly exhibited bright green light emission under normal daylight conditions, without the need for excitation with UV light. Similar results were observed for cells transformed with the A3 mutant GFP. Cells containing the A1 and A5 mutant GFPs were also seen to be less (but still observably) fluorescent under white light illumination. Conversely, only very weak emission of light was observed under white light illumination in the cells transformed with the vectors comprising only the S65T, A2 and A9 mutations. Cells comprising the A6, A7 and A8 mutations exhibited no fluorescence when illuminated by white light.

When plates containing these mutants were stored in the dark at 4° C. for 38 days, however, all of the colonies except those containing the A6, A7 or A8 mutant GFPs were seen to be more intensely fluorescent under white light illumination. Colonies containing the A3, A4 and A5 mutants were more fluorescent under these conditions than were those containing the A1, A2, A9 and S65T mutants, although all colonies fluoresced more brightly than they did in freshly plated cells (i.e., when observed within 24–48 hours of transfection). When these plates were allowed to warm to room temperature, the fluorescence in colonies containing the A1, A2, A9 and S65T mutants decreased, while that in colonies containing the A3, A4 and A5 mutants remained brightly fluorescent.

It is possible that the increased fluorescence observed in stored plates may have been due to accumulation of mutant protein in the cells over time in storage, indicating a dependence of white light fluorescence upon intracellular concentration of the GFP. To test this notion, a 6His-tagged A4 GFP construct prepared and isolated by metal affinity chromatography according to standard techniques (see Ausubel, F. M., et al., in *Current Protocols in Molecular Biology*, New York: John Wiley & Sons, Inc., pp. 10.11.10–10.11.24 (1996)), was examined for fluorescence under blue, red and white light at various protein concentrations in solution. At a concentration of about 1.5 μg/ml, the purified A4 GFP was brightly fluorescent under sunlight and fluorescent indoor white lighting, as well as under blue light; no fluorescence was observed, however, under red light. This highly concentrated A4 GFP solution became nonfluorescent upon boiling, but was at least slightly fluorescent up to a temperature of about 82° C. When diluted to 0.1 μg/ml, however, the A4 GFP solution fluoresced brightly under blue light (closer in wavelength to the excitation maximum of GFP which is in the UV range), but did not fluoresce under white light illumination. These results suggest that the increased fluorescence observed upon white light illumination of colonies stored for extended periods of time may be due to accumulation of GFP protein in the cells.

Taken together, these results indicate that prokaryotic cells containing the A3 or A4 mutant GFPs, and to a lesser extent the A1 and A5 mutant GFPs, can emit light without the addition of an exogenous substrate or the use of ultraviolet irradiation. Use of these GFP constructs thus provides advantages over other visible light reporter vectors which require the use of exogenous substrates, and over other fluorescent reporter vectors which require UV irradiation which may induce undesirable mutations in the host cells.

Example 6

Additional GFP Mutations

To examine the effects of alternative point mutations on GFP fluorescence, mutations are targeted at the tryptophan residue at position 67 (the only tryptophan residue in the entire GFP molecule which is located in the unique motif Pro-Val-Pro-Trp-Pro (SEQ ID NO:17)). To accomplish this mutation, oligonucleotides are designed to mutate Trp57→His or Trp57→Tyr, in conjunction with the Ser65→Thr mutant (SEQ ID NO:4) or the Phe64→Met; Ser65→Ala mutant (SEQ ID NO:6). These mutants are made in the bacterial vector pProEX HTb as described in Example 4, using specific oligonucleotides designed to provide the desired mutations. The vector constructs are then transfected into host cells and characterized as above for their fluorescence.

In a similar fashion, mutations are made at other amino acid positions outside of the GFP chromophore region. For example, mutations are made at Arg96, which is probably responsible for stabilizing resonance structures of the imidazolidone 5-membered ring during ring formation and possibly during excitation, and is therefore a target for more rapid ring formation and, hence, faster detection of fluorescence. Mutations involving this residue include Arg96→His.

Mutations are also possible at Phe46, which along with Phe64 separates the 5-membered chromophore ring from direct contact with the single tryptophan in the Ser65→Thr GFP (SEQ ID NO:4). By allowing direct hydrogen bonding between Trp57 and the ring structure, efficient energy transfer is possible as with the Phe64→Leu; Ser64→Thr mutant. Mutations involving this residue include Phe46→Leu or other hydrophobic residues that promote hydrogen bonding.

Mutations are also made at Leu221 and Phe223, which are involved in dimer formation. Only three hydrophobic residues are in the dimer contact region; all others are hydrophobic. By mutating Leu221 and/or Phe223 to a hydrophilic or "neutral" residue such as glycine, GFP aggregation, which can be a problem with GFP fusion constructs, may be inhibited.

Mutations are also made at His148, which probably stabilizes the fluorophore and forms hydrogen bonds with Tyr66 and Gln94. Mutations of His148 to a residue with a different charge or a different pKa are made to allow alteration of the excitation and emission spectra of GFP, similar to results seen with Tyr66→His which results in blue fluorescence by GFP.

Finally, mutations introducing a second 5-membered ring structure into the α-helix of GFP are made, to allow increased fluorescence intensity of the resultant GFP.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A nucleic acid molecule encoding a mutant Green Fluorescent Protein (GFP), mutated at amino acid positions corresponding the amino acid positions 64 and 65 of SEQ ID NO:4 by substitution mutations that are selected from the group consisting of:
   (a) a cysteine residue substituted for the phenylalanine residue at the amino acid position corresponding to amino acid position 64 of SEQ ID NO:4, and an alanine residue substituted for the serine residue at the amino acid position corresponding to amino acid position 65 of SEQ ID NO:4; and
   (b) a methionine residue substituted for the phenylalanine residue at the amino acid position corresponding to amino acid position 64 of SEQ ID NO:4, and an alanine residue substituted for the serine residue at the amino acid position corresponding to amino acid position 65 of SEQ ID NO:4.

2. A nucleic acid molecule encoding a mutant Green Fluorescent Protein (GFP), wherein said mutant GFP has an amino acid sequence as set forth in SEQ ID NO:5.

3. A nucleic acid molecule encoding a mutant Green Fluorescent Protein (GFP), wherein said mutant GFP has an amino acid sequence as set forth in SEQ ID NO:6.

4. A host cell comprising the nucleic acid molecule of anyone of claims 1–3.

5. A vector comprising the nucleic acid molecule of any one of claims 1–3.

6. The vector of claim 5, wherein said vector is an expression vector.

7. A host cell comprising the vector of claim 5.

8. A method for producing a mutant Green Fluorescent Protein (GFP), comprising culturing the host cell of claim 4 under conditions favoring the production of a mutant GFP, and isolating said mutant GFP from said host cell.

9. A method for producing a mutant Green Fluorescent Protein (GFP), comprising culturing the host cell of claim 7 under conditions favoring the production of a mutant GFP, and isolating said mutant GFP from said host cell.

10. A composition comprising the nucleic acid molecule of any one of claims 1–3.

11. A kit comprising at least one container containing the nucleic acid molecule of any one of claims 1–3.

12. The kit of claim 11, further comprising at least one additional container containing a reagent for delivering said nucleic acid molecule into a host cell.

13. The kit of claim 12, wherein said reagent for delivering said nucleic acid molecule into a host cell comprises a liposome.

14. A humanized nucleic acid molecule encoding a mutant Green Fluorescent Protein (GFP), mutated at amino acid positions corresponding the amino acid positions 64 and 65 of SEQ ID NO:4 by substitution mutations that are selected from the group consisting of:
   (a) a cysteine residue substituted for the phenylalanine residue at the amino acid position corresponding to amino acid position 64 of SEQ ID NO:4, and an alanine residue substituted for the serine residue at the amino acid position corresponding to amino acid position 65 of SEQ ID NO:4; and (b) a methionine residue substituted for the phenylalanine residue at the amino acid position corresponding to amino acid position 64 of SEQ ID NO:4, and an alanine residue substituted for the serine residue at the amino acid position corresponding to amino acid position 65 of SEQ ID NO:4.

15. A host cell comprising the nucleic acid molecule of claim 14.

16. A vector comprising the nucleic acid molecule of claim 14.

17. The vector of claim 16, wherein said vector is an expression vector.

18. A host cell comprising the vector of claim 16.

19. A method for producing a mutant Green Fluorescent Protein (GFP), comprising culturing the host cell of claim 15 or claim 18 under conditions favoring the production of a mutant GFP, and isolating said mutant GFP from said host cell.

20. A composition comprising the nucleic acid molecule of claim 14.

21. A kit comprising at least one container containing the nucleic acid molecule of claim 14.

22. The kit of claim 21, further comprising at least one additional container containing a reagent for delivering said nucleic acid molecule into a host cell.

23. The kit of claim 22, wherein said reagent for delivering said nucleic acid molecule into a host cell comprises a liposome.

* * * * *

SEQUENCE LISTING

<160> NUMBER OF SEQ ID NOS: 17

<210> SEQ ID NO 1
<211> LENGTH: 717
<212> TYPE: DNA
<213> ORGANISM: Aequorea victoria, gfp(h) S65T mutant cDNA clone

<400> SEQUENCE: 1

```
atg agc aag ggc gag gaa ctg ttc act ggc gtg gtc cca att ctc gtg      48
Met Ser Lys Gly Glu Glu Leu Phe Thr Gly Val Val Pro Ile Leu Val
 1               5                  10                  15 gaa ctg gat ggc gat gtg aat ggg cac aaa ttt tct gtc agc gga gag      96
Glu Leu Asp Gly Asp Val Asn Gly His Lys Phe Ser Val Ser Gly Glu
            20                  25                  30 ggt gaa ggt gat gcc aca tac gga aag ctc acc ctg aaa ttc atc tgc     144
Gly Glu Gly Asp Ala Thr Tyr Gly Lys Leu Thr Leu Lys Phe Ile Cys
        35                  40                  45 acc act gga aag ctc cct gtg cca tgg cca aca ctg gtc act acc ttc     192
Thr Thr Gly Lys Leu Pro Val Pro Trp Pro Thr Leu Val Thr Thr Phe
    50                  55                  60 acc tat ggc gtg cag tgc ttt tcc aga tac cca gac cat atg aag cag     240
Thr Tyr Gly Val Gln Cys Phe Ser Arg Tyr Pro Asp His Met Lys Gln
65                  70                  75                  80 cat gac ttt ttc aag agc gcc atg ccc gag ggc tat gtg cag gag aga     288
His Asp Phe Phe Lys Ser Ala Met Pro Glu Gly Tyr Val Gln Glu Arg
                85                  90                  95 acc atc ttt ttc aaa gat gac ggg aac tac aag acc cgc gct gaa gtc     336
Thr Ile Phe Phe Lys Asp Asp Gly Asn Tyr Lys Thr Arg Ala Glu Val
            100                 105                 110 aag ttc gaa ggt gac acc ctg gtg aat aga atc gag ttg aag ggc att     384
Lys Phe Glu Gly Asp Thr Leu Val Asn Arg Ile Glu Leu Lys Gly Ile
        115                 120                 125 gac ttt aag gaa gat gga aac att ctc ggc cac aag ctg gaa tac aac     432
Asp Phe Lys Glu Asp Gly Asn Ile Leu Gly His Lys Leu Glu Tyr Asn
    130                 135                 140 tat aac tcc cac aat gtg tac atc atg gcc gac aag caa aag aat ggc     480
Tyr Asn Ser His Asn Val Tyr Ile Met Ala Asp Lys Gln Lys Asn Gly
```

```
                145                 150                 155                 160
atc aag gtc aac ttc aag atc aga cac aac att gag gat gga tcc gtg        528
Ile Lys Val Asn Phe Lys Ile Arg His Asn Ile Glu Asp Gly Ser Val
                165                 170                 175 cag ctg gcc gac cat tat caa cag aac act cca atc ggc gac ggc cct        576
Gln Leu Ala Asp His Tyr Gln Gln Asn Thr Pro Ile Gly Asp Gly Pro
                180                 185                 190 gtg ctc ctc cca gac aac cat tac ctg tcc acc cag tct gcc ctg tct        624
Val Leu Leu Pro Asp Asn His Tyr Leu Ser Thr Gln Ser Ala Leu Ser
                195                 200                 205 aaa gat ccc aac gaa aag aga gac cac atg gtc ctg ctg gag ttt gtg        672
Lys Asp Pro Asn Glu Lys Arg Asp His Met Val Leu Leu Glu Phe Val
                210                 215                 220 acc gct gct ggg atc aca cat ggc atg gac gag ctg tac aag                714
Thr Ala Ala Gly Ile Thr His Gly Met Asp Glu Leu Tyr Lys
225                 230                 235 tga                                                                    717
```

<210> SEQ ID NO 2
<211> LENGTH: 238
<212> TYPE: PRT
<213> ORGANISM: Aequorea victoria, gfp(h) S65T mutant cDNA clone

<400> SEQUENCE: 2

```
Met Ser Lys Gly Glu Glu Leu Phe Thr Gly Val Val Pro Ile Leu Val
 1               5                  10                  15

Glu Leu Asp Gly Asp Val Asn Gly His Lys Phe Ser Val Ser Gly Glu
                20                  25                  30

Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Phe
        50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235
```

<210> SEQ ID NO 3

<211> LENGTH: 717
<212> TYPE: DNA
<213> ORGANISM: Aequorea victoria, gfp10 cDNA clone

<400> SEQUENCE: 3

| | | | | | | | | | | | | | | | | |
|---|---|---|---|---|---|---|---|---|---|---|---|---|---|---|---|---|
| atg | agt | aaa | gga | gaa | gaa | ctt | ttc | act | gga | gtt | gtc | cca | att | ctt | gtt | 48 |
| Met | Ser | Lys | Gly | Glu | Glu | Leu | Phe | Thr | Gly | Val | Val | Pro | Ile | Leu | Val | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gaa | tta | gat | ggt | gat | gtt | aat | ggg | cac | aaa | ttt | tct | gtc | agt | gga | gag | 96 |
| Glu | Leu | Asp | Gly | Asp | Val | Asn | Gly | His | Lys | Phe | Ser | Val | Ser | Gly | Glu | |
| | | | 20 | | | | | 25 | | | | | 30 | | | |

| | | | | | | | | | | | | | | | | |
|---|---|---|---|---|---|---|---|---|---|---|---|---|---|---|---|---|
| ggt | gaa | ggt | gat | gca | aca | tac | gga | aaa | ctt | acc | ctt | aaa | ttt | att | tgc | 144 |
| Gly | Glu | Gly | Asp | Ala | Thr | Tyr | Gly | Lys | Leu | Thr | Leu | Lys | Phe | Ile | Cys | |
| | | 35 | | | | | 40 | | | | | 45 | | | | |

| | | | | | | | | | | | | | | | | |
|---|---|---|---|---|---|---|---|---|---|---|---|---|---|---|---|---|
| act | act | gga | aaa | cta | cct | gtt | cca | tgg | cca | aca | ctt | gtc | act | act | ttc | 192 |
| Thr | Thr | Gly | Lys | Leu | Pro | Val | Pro | Trp | Pro | Thr | Leu | Val | Thr | Thr | Phe | |
| 50 | | | | | 55 | | | | | 60 | | | | | | |

| | | | | | | | | | | | | | | | | |
|---|---|---|---|---|---|---|---|---|---|---|---|---|---|---|---|---|
| tct | tat | ggt | gtt | caa | tgc | ttt | tca | aga | tac | cca | gat | cat | atg | aaa | cag | 240 |
| Ser | Tyr | Gly | Val | Gln | Cys | Phe | Ser | Arg | Tyr | Pro | Asp | His | Met | Lys | Gln | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| cat | gac | ttt | ttc | aag | agt | gcc | atg | ccc | gaa | ggt | tat | gta | cag | gaa | aga | 288 |
| His | Asp | Phe | Phe | Lys | Ser | Ala | Met | Pro | Glu | Gly | Tyr | Val | Gln | Glu | Arg | |
| | | | | 85 | | | | | 90 | | | | | 95 | | |

| | | | | | | | | | | | | | | | | |
|---|---|---|---|---|---|---|---|---|---|---|---|---|---|---|---|---|
| act | ata | ttt | ttc | aaa | gat | gac | ggg | aac | tac | aag | aca | cgt | gct | gaa | gtc | 336 |
| Thr | Ile | Phe | Phe | Lys | Asp | Asp | Gly | Asn | Tyr | Lys | Thr | Arg | Ala | Glu | Val | |
| | | | 100 | | | | | 105 | | | | | 110 | | | |

| | | | | | | | | | | | | | | | | |
|---|---|---|---|---|---|---|---|---|---|---|---|---|---|---|---|---|
| aag | ttt | gaa | ggt | gat | acc | ctt | gtt | aat | aga | atc | gag | tta | aaa | ggt | att | 384 |
| Lys | Phe | Glu | Gly | Asp | Thr | Leu | Val | Asn | Arg | Ile | Glu | Leu | Lys | Gly | Ile | |
| | | 115 | | | | | 120 | | | | | 125 | | | | |

| | | | | | | | | | | | | | | | | |
|---|---|---|---|---|---|---|---|---|---|---|---|---|---|---|---|---|
| gat | ttt | aaa | gaa | gat | gga | aac | att | ctt | gga | cac | aaa | ttg | gaa | tac | aac | 432 |
| Asp | Phe | Lys | Glu | Asp | Gly | Asn | Ile | Leu | Gly | His | Lys | Leu | Glu | Tyr | Asn | |
| 130 | | | | | 135 | | | | | 140 | | | | | | |

| | | | | | | | | | | | | | | | | |
|---|---|---|---|---|---|---|---|---|---|---|---|---|---|---|---|---|
| tat | aac | tca | cac | aat | gta | tac | atc | atg | gca | gac | aaa | caa | aag | aat | gga | 480 |
| Tyr | Asn | Ser | His | Asn | Val | Tyr | Ile | Met | Ala | Asp | Lys | Gln | Lys | Asn | Gly | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| atc | aaa | gtt | aac | ttc | aaa | att | aga | cac | aac | att | gaa | gat | gga | agc | gtt | 528 |
| Ile | Lys | Val | Asn | Phe | Lys | Ile | Arg | His | Asn | Ile | Glu | Asp | Gly | Ser | Val | |
| | | | | 165 | | | | | 170 | | | | | 175 | | |

| | | | | | | | | | | | | | | | | |
|---|---|---|---|---|---|---|---|---|---|---|---|---|---|---|---|---|
| caa | cta | gca | gac | cat | tat | caa | caa | aat | act | cca | att | ggc | gat | ggc | cct | 576 |
| Gln | Leu | Ala | Asp | His | Tyr | Gln | Gln | Asn | Thr | Pro | Ile | Gly | Asp | Gly | Pro | |
| | | | 180 | | | | | 185 | | | | | 190 | | | |

| | | | | | | | | | | | | | | | | |
|---|---|---|---|---|---|---|---|---|---|---|---|---|---|---|---|---|
| gtc | ctt | tta | cca | gac | aac | cat | tac | ctg | tcc | aca | caa | tct | gcc | ctt | tcg | 624 |
| Val | Leu | Leu | Pro | Asp | Asn | His | Tyr | Leu | Ser | Thr | Gln | Ser | Ala | Leu | Ser | |
| | | 195 | | | | | 200 | | | | | 205 | | | | |

| | | | | | | | | | | | | | | | | |
|---|---|---|---|---|---|---|---|---|---|---|---|---|---|---|---|---|
| aaa | gat | ccc | aac | gaa | aag | aga | gac | cac | atg | gtc | ctt | ctt | gag | ttt | gta | 672 |
| Lys | Asp | Pro | Asn | Glu | Lys | Arg | Asp | His | Met | Val | Leu | Leu | Glu | Phe | Val | |
| | | 210 | | | | | 215 | | | | | 220 | | | | |

| | | | | | | | | | | | | |
|---|---|---|---|---|---|---|---|---|---|---|---|---|
| aca | gct | gct | ggg | att | aca | cat | ggc | atg | gat | gaa | cta | tac | aaa | 714 |
| Thr | Ala | Ala | Gly | Ile | Thr | His | Gly | Met | Asp | Glu | Leu | Tyr | Lys | |
| 225 | | | | | 230 | | | | | 235 | | | | |

| | |
|---|---|
| taa | 717 |

<210> SEQ ID NO 4
<211> LENGTH: 238
<212> TYPE: PRT
<213> ORGANISM: Aequorea victoria, gfp10 cDNA clone

<400> SEQUENCE: 4

| | | | | | | | | | | | | | | | |
|---|---|---|---|---|---|---|---|---|---|---|---|---|---|---|---|
| Met | Ser | Lys | Gly | Glu | Glu | Leu | Phe | Thr | Gly | Val | Val | Pro | Ile | Leu | Val |
| 1 | | | | 5 | | | | | 10 | | | | | 15 | |

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
            85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
        130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 5
<211> LENGTH: 238
<212> TYPE: PRT
<213> ORGANISM: Aequorea victoria, A1 mutant

<400> SEQUENCE: 5

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Cys
    50                  55                  60

Ala Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
            85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
        130                 135                 140

Tyr Asn Ser His Asn Val Tyr Ile Met Ala Asp Lys Gln Lys Asn Gly
145                 150                 155                 160

```
Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
210                 215                 220

Thr Ala Ala Gly Ile Thr His Gly Met Asp Glu Leu Tyr Lys
225                 230                 235

<210> SEQ ID NO 6
<211> LENGTH: 238
<212> TYPE: PRT
<213> ORGANISM: Aequorea victoria, A4 mutant

<400> SEQUENCE: 6

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Met
    50                  55                  60

Ala Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
210                 215                 220

Thr Ala Ala Gly Ile Thr His Gly Met Asp Glu Leu Tyr Lys
225                 230                 235

<210> SEQ ID NO 7
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 7
```

-continued caacacuggu cacuacctgc gcctatggcg tgc                     33

<210> SEQ ID NO 8
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 8
ccaacacugg ucacuaccug cacctatgg                          29

<210> SEQ ID NO 9
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 9
caacacuggu cacuaccctc acctatggcg tgcagt                  36

<210> SEQ ID NO 10
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 10
caacacuggu cacuacaatg gcctatggcg tgcagtgct               39

<210> SEQ ID NO 11
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 11
caacacuggu cacuaccatg acctatggcg tgcagtgct               39

<210> SEQ ID NO 12
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 12
caacacuggu cacuaccatg ttcttcggcg tgcagtgct               39

<210> SEQ ID NO 13
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 13
caacacuggu cacuaccatg ttcaagggcg tgcagtgct               39

<210> SEQ ID NO 14
<211> LENGTH: 36
<212> TYPE: DNA
<213> ORGANISM: Artificial sequence

```
<220> FEATURE:
<223> OTHER INFORMATION: Synthetic oligonucleotide

<400> SEQUENCE: 14
caacacuggu cacuaccaca tgctatggcg tgcagt                                   36

<210> SEQ ID NO 15
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 15
caacacuggu cacuaccgtg tgctatggcg tgcagt                                   36

<210> SEQ ID NO 16
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 16
agugaccagu guuggccaag gcacagggag ctt                                      33

<210> SEQ ID NO 17
<211> LENGTH: 5
<212> TYPE: PRT
<213> ORGANISM: Aequorea victoria

<400> SEQUENCE: 17

Pro Val Pro Trp Pro
1               5
```